United States Patent
Meylan et al.

(10) Patent No.: US 10,636,834 B2
(45) Date of Patent: Apr. 28, 2020

(54) PHOTON COUNTING CONE-BEAM CT APPARATUS WITH MONOLITHIC CMOS INTEGRATED PIXEL DETECTORS

(71) Applicant: G-ray Switzerland SA, Hauterive NE (CH)

(72) Inventors: Claude Meylan, Saint-Aubin-Sauges (CH); Hans Von Känel, Wallisellen (CH)

(73) Assignee: G-ray Switzerland SA, Haulerive (CH)

( * ) Notice: Subject to any disclaimer, the term of this patent is extended or adjusted under 35 U.S.C. 154(b) by 0 days.

(21) Appl. No.: 15/754,597

(22) PCT Filed: Aug. 31, 2016

(86) PCT No.: PCT/IB2016/001232
§ 371 (c)(1),
(2) Date: Feb. 23, 2018

(87) PCT Pub. No.: WO2017/037527
PCT Pub. Date: Mar. 9, 2017

(65) Prior Publication Data
US 2018/0240842 A1    Aug. 23, 2018

Related U.S. Application Data

(60) Provisional application No. 62/211,958, filed on Aug. 31, 2015, provisional application No. 62/295,720, filed on Feb. 16, 2016.

(30) Foreign Application Priority Data

Dec. 21, 2015   (WO) .................. PCT/IB2015/002385

(51) Int. Cl.
*A61B 6/00* (2006.01)
*H01L 27/146* (2006.01)
(Continued)

(52) U.S. Cl.
CPC .......... *H01L 27/14661* (2013.01); *A61B 6/03* (2013.01); *A61B 6/032* (2013.01);
(Continued)

(58) Field of Classification Search
CPC ...... A61B 6/4085; A61B 6/4241; A61B 6/502
See application file for complete search history.

(56) References Cited

U.S. PATENT DOCUMENTS

| 5,712,484 A | 1/1998 | Harada et al. |
| 6,787,885 B2 | 9/2004 | Esser et al. |

(Continued)

FOREIGN PATENT DOCUMENTS

| EP | 0 571 135 A2 | 11/1993 |
| EP | 1 691 422 A1 | 8/2006 |

(Continued)

OTHER PUBLICATIONS

Alig, R. C. et al; Scattering by ionization and phonon emission in semiconductors, Physical Review B, vol. 22, No. 12, Dec. 15, 1980, p. 5565-5582, The American Physical Society.

(Continued)

*Primary Examiner* — Dani Fox
(74) *Attorney, Agent, or Firm* — Da Vinci Partners LLC; John Moetteli

(57) ABSTRACT

CBCT including monolithic photon counting FPD for medical applications requiring real-time 3D imaging, like mammography, interventional guided procedures or external beam radiotherapy, includes CMOS processed readout electronics monolithically integrated with a single crystalline X-ray absorber by covalent wafer bonding near room temperature and adapted for single photon counting providing high energy, temporal and spatial resolution.

22 Claims, 12 Drawing Sheets

(51) Int. Cl.
*A61B 6/03* (2006.01)
*H01L 23/00* (2006.01)

(52) U.S. Cl.
CPC .......... *A61B 6/4085* (2013.01); *A61B 6/4233* (2013.01); *A61B 6/4241* (2013.01); *A61B 6/4441* (2013.01); *A61B 6/502* (2013.01); *A61B 6/504* (2013.01); *H01L 24/16* (2013.01); *H01L 27/1469* (2013.01); *H01L 27/14634* (2013.01); *H01L 27/14636* (2013.01); *H01L 27/14659* (2013.01); *H01L 27/14689* (2013.01)

(56) References Cited

U.S. PATENT DOCUMENTS

| | | | |
|---|---|---|---|
| 8,237,126 | B2 | 8/2012 | Von Känel et al. |
| 8,378,310 | B2 | 2/2013 | Bornefalk et al. |
| 8,792,965 | B2 | 7/2014 | Ning et al. |
| 2014/0226783 | A1* | 8/2014 | Ning ...................... A61B 6/032 378/5 |
| 2016/0209521 | A1* | 7/2016 | Jakubek ................ G01T 1/2928 |

FOREIGN PATENT DOCUMENTS

| | | |
|---|---|---|
| WO | 02/067271 A2 | 8/2002 |
| WO | 2008/117720 A2 | 11/2006 |
| WO | 2011/102779 A1 | 8/2011 |
| WO | 2011/135432 A1 | 11/2011 |
| WO | 2014/123726 A1 | 8/2014 |

OTHER PUBLICATIONS

Alig, R. Casanova; Scattering by ionization and phonon emission in semiconductors, II. Monte Carlo calculations; Physical Review B, vol. 27, No. 2, Jan. 15, 1983, p. 968-977, The American Physical Society.
Baba, Rika et al; Comparison of flat-panel detector and image-intensifier detector for cone-beam CT, Computerized Medical Imaging and Graphics 26, 2002, p. 153-158, Elsevier Science Ltd.
Bale, Derek S. et al; Nature of polarization in wide-bandgap semiconductor detectors under high-flux irradiation: Application to semi-insulating Cd Zn Te, Physical Review B 77, 2008, p. 035205-1 to 035205-16, The American Physical Society.
Ballabriga, R. et al; The Medipix3RX: a high resolution, zero dead-time pixel detector readout chip allowing spectroscopic imaging; Sissa Medilab, Feb. 8, 2013, CERN.
Bertolucci, E. et al; GaAs pixel radiation detector as an autoradiography tool for genetic studies, Nuclear Instruments and Methods in Physics Research A 422, 1999, p. 242-246, Elsevier Science B.V.
Bornefalk, Hans et al; Photon-counting spectral computed tomography using silicon strip detectors: a feasability study, Physics in Medicine and Biology 55, 2010, p. 1999-2022, Institute of Physics and Engineering in Medicine.
Cho, Hyo-Min et al; Characteristic performance evaluation of a photon counting Si strip detector for low dose spectral breast CT imaging, Med. Phys. 41 (9), Sep. 2014, p. 091903-1 to 091903-10, Am. Assoc. Phys. Med.
Colace, L. et al; Low Dark-Current Germanium-on-Silicon Near-Infrared Detectors, IEEE Photonics Technology Letters, vol. 19, No. 22, Nov. 15, 2007, p. 1813-1815, IEEE.
Falub, Claudiu V. et al; Perfect crystals grown from imperfect interfaces, Scientific Reports 3 2276, Jul. 24, 2013, p. 1-6.
Fitzgerald, E. A. et al; Totally relaxed GeSi-layers with low threading dislocation densities grown on Si substrates, Appl. Phys. Lett. 59 (7), Aug. 12, 1991, p. 811-813, American Institute of Physics.
Flötgen, C. et al; Novel Surface Preparation Methods for Covalent and Conductive Bonded Interfaces Fabrication, ECS Transactions 64 (5), 2014, p. 103-110, The Electrochemical Society.

Gros D'Aillon, Eric et al; Development and characterization of a 3D GaAs X-ray detector for medical imaging, Nuclear Instruments and Methods in Physics Research A 727, 2013, p. 126-130, Elsevier B.V.
Gupta, Rajiv et al; Ultra-high resolution flat-panel volume CT: fundamental principles, design architecture, and system characterization, Eur. Radiol. 16, 2006, p. 1191-1205.
Hamann, Elias et al; Performance of a Medipix3RX Spectroscopic Pixel Detector With a High Resistivity Gallium Arsenide Sensor, IEEE Transactions on Medical Imaging, vol. 34, No. 3, Mar. 2015, p. 707-715, IEEE.
Henry, D. et al; TSV Last for Hybrid Pixel Detectors: Application to Particle Physics and Imaging Experiments, IEEE Electronic Components and Technology Conference, 2013, p. 568-575, IEEE.
Hirota, Shozo et al; Cone-Beam CT with Flat-Panel-Detector Digital Angiography System: Experience in Abdominal Interventional Procedures, CardioVascular and Interventional Radiology 29, 2006, p. 1034-1038, Springer Science + Business Media, Inc.
Isa, Fabio et al; From plastic to elastic stress relaxation in highly mismatched SiGe/Si heterostructures, Acta Materialia 114, 2016, p. 97-105, Elsevier Ltd.
Jiang, Tingting et al; Hydrogenation of interface states at a clean grain boundary in the direct silicon bonded wafer, Phys. Status Solidi A 209, 2012, p. 990-993, Wiley-VCH Verlag GmbH & Co. KGaA.
Kasap, Safe et al; Amorphous and Polycrystalline Photoconductors for Direct Conversion Flat Panel X-ray Image Sensors, Sensors 11, 2011, p. 5112-5157.
Klaasen, Erno H. et al; Silicon fusion bonding and deep reactive ion etching: a new technology for microstructures, Sensors ans Actuators A 52, 1996, p. 132-139, Elsevier ɛcience 3.A.
Kreiliger, Thomas et al; Individual heterojunctions of 3D germanium crystals on silicon CMOS for monolithically integrated X-ray detector, Physica Status Solidi A 211, 2014, p. 131-135, Wiley-VCH Verlag GmbH & Co. KGaA.
Liu, Xuejin et Al; A Silicon-Strip Detector for Photon-Counting Spectral CT: Energy Resolution From 40 keV to 120 keV, IEEE Transactions on Nuclear Science, vol. 61, No. 3, Jun. 2014, p. 1099-1105 , IEEE.
Loshachenko, Anton et al; Impact of hydrogen on electrical levels and luminescence of dislocation network at the interface of hydrophilically bonded silicon wafers, Phys. Status Solidi C 10, 2013, p. 36-39, Wiley-VCH Verlag GmbH & Co. KGaA.
Mattiazzo, S. et al; LePIX: First results from a novel monolithic pixel sensor, Nuclear Instruments and Methods in Physics Research, A 718, 2013, p. 288-291, Elsevier B.V.
Orth, Robert C. et al; C-arm Cone-beam CT: General Principles and Technical Considerations for Use in Interventional Radiology, J. Vasc. Interv. Radiol. 19, 2008, p. 814-821, SIR.
Pennicard, David et al; Development of LAMBDA: Large Area Medipix-Based Detector Array, JINST 6 C11009, 2012, IOP Publishing Ltd and SISSA.
Procz, Simon et al; Medipix3 CT for material sciences, JINST 8 C01025, 2013, IOP Publishing Ltd and SISSA Medialab srl.
Salvalaglio, Marco et al; Fine control of plastic and elastic relaxation in Ge/Si vertical heterostructures, Journal of Applied Physics 116, 2014, p. 104306-1 to 104306-9, American Institute of Physics.
Sechopoulos, Ioannis; A review of breast tomosynthesis. Part 1. The image acquisition process, Med. Phys. 40 (1), Jan. 2013, p. 014301-1 to 014301-12, Am. Assoc. Phys. Med.
Taguchi Katsuyuki et al; Vision 20/20: Single photon counting x-ray detectors in medical imaging, Medical Physics 40 (10), Oct. 2013, p. 100901-1 to 100901-19, Am. Assoc. Phys. Med.
Veale, M.C. et al; Chromium compensated gallium arsenide detectors for X-ray and y-ray spectroscopic imaging, Nuclear Instruments and Methods in Physics Research A 752, 2014, p. 0-14, Elsevier B.V.
Vykydal, Zdenek et al; The RELAXd project: Development of four-side tilable photon-counting imagers, Nuclear Instruments and Methods in Physics Research A 591, 2008, p. 241-244, Elsevier B.V.
Weber, J. et al; Near-band-gap photoluminescence of Si—Ge alloys,

(56) References Cited

OTHER PUBLICATIONS

Physical Review B, vol. 40, No. 8, Sep. 15, 1989, p. 5683-5693, The American Physical Society.

* cited by examiner

Structure Code:

▨ Active Volume
━━━ Implanted or Barrier Contact (P +)
━ ━ ━ Diffused Contact (N +)
- - - - Passive Surface

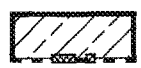
Ultra LEGe
Low Energy
Responce High
Resolution
Peak Shape

LEGe
Large Area
Thin Window
High Resolution

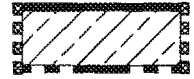
BEGe
Broad Energy Range
High Efficiency High
Resolution Thin
Window

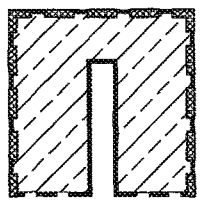
Coaxial Ge
High Efficiency
High Resolution

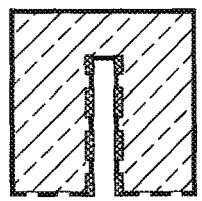
REGe
Thin Window
Neutron Damage
Resisitant

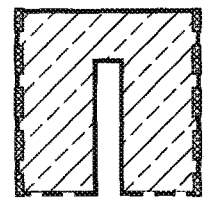
XtRa
Thin Window
High Efficiency

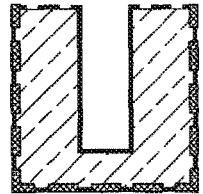
Well
4p Counting
High Efficiency

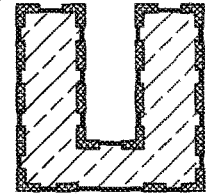
SAGe Well
Thin Window
4p Counting
High Efficiency
High Resolution

Detector Type:

Ultra LEGe Germanium
    Low Energy Germanium
        Broad Energy Germanium
            Coaxial Germanium
        Reverse-Electrode (REGe) and XtRa
            Germanium Well
                Small Anode Germanium Well 0    1    10    100    1000    10000
Energy (keV)

FIG. 10

| Experimental Results with Detector Model GC-1019 | | |
|---|---|---|
| Resistor Value | $^{57}$Co (122 keV FWHM) | $^{60}$Co (1332 keV FWHM) |
| 2 Gogom | | 1.81 |

PHOTON COUNTING CONE-BEAM CT APPARATUS WITH MONOLITHIC CMOS INTEGRATED PIXEL DETECTORS

CROSS REFERENCE TO RELATED APPLICATIONS

This application is the National Stage of International Application No. PCT/IB2016/001232, filed Aug. 31, 2016, which claims benefit under 35 USC § 119(a), to PCT application No. PCT/IB2015/002385, filed Dec. 21, 2015, and under § 119(e) to U.S. Provisional Application No. 62/211,958, filed 31 Aug. 2015 and to U.S. Provisional Application No. 62/295,720, filed Feb. 16, 2016.

FIELD OF THE INVENTION

The invention relates to computed tomography (CT) imaging equipment and more specifically to cone beam computer tomography (CBCT) with monolithically integrated semiconductor detectors with energy discriminating capabilities.

BACKGROUND OF THE INVENTION

Many medical applications requiring 3D real-time X-ray imaging, like angiographic interventions including vascular stent and stent graft placements, transcatheter embolization and targeted intravascular oncologic procedures, or non-angiographic procedures such as image guided orthopedic, thoracic, abdominal, head and neck, and neuro surgery, biopsies, brachytherapy or external beam radiotherapy, percutaneous drain and stent placement or radiofrequency ablation, could be enhanced by the availability of a faster, more efficient and higher resolution detector. Patients' radiations dose absorption remains obviously a major concern and should be reduced as far as possible.

Also breast imaging requires high resolution at an efficient use of radiation dose for reliable detection of calcifications and delineation of soft tissues still unmet with current imaging technologies. In this field of applications, a trend towards 3D imaging is also observed (see for example I. Sechopoulos in Med Phys. (2013); 40 (1)014302, the entire disclosures of which are hereby incorporated by reference). Tomosynthesis is one of these new imaging technology that fuses CBCT reconstruction with digital image processing to generate images of specified cross sections from a single tomography scan. These devices may as well be much improved with the help of new more efficient detectors.

Flat-panel detectors (FPD) are widely used for medical imaging and have critically increased safety of minimally invasive and endovascular procedures, however, at the price of increased patient and operator irradiation because of limited detection efficiency. There are two fundamentally different designs of FPD. The first (I) is based on indirect conversion, i.e. a two-stage process in which X-rays incident on an absorption layer are transformed to visible photons which are then detected by ordinary photodetectors. The second design (II) rests on the direct conversion of X-rays into electrical signals within a semiconducting absorption layer.

The physics of indirect detectors remains essentially unchanged from that of medical X-ray image intensifiers (XII), which have dominated real time radiographic imaging for over fifty years. The conversion of X-ray photons into visible photons takes place in a scintillation layer such as CsI(T1). Apart from limited spatial and energy resolution, the two-stage conversion process suffers from the drawback of low conversion efficiency and limited spectral resolution. The efficiency of wavelength conversion in CsI(TI), for example, may be around 10% and the subsequent conversion of the visible light into electron-hole (e-h) pairs in the photodetectors typically has an efficiency below 50%. As a result, the number of electron-hole pairs collected by the readout circuit is on the order of 25 per keV of X-ray energy (see U.S. Pat. No. 8,237,126 to H. von Känel, the entire disclosure of which is hereby incorporated by reference).

These drawbacks are essentially absent in direct detection of X-rays by means of semiconductor absorbers in which X-rays are converted into electron-hole (e-h) pairs giving rise to electrical signals. For reasons of manufacturability and costs, current devices are, however, based on polycrystalline or amorphous materials and readout circuits made from thin film transistors. Such FPD can be produced in a monolithic form, wherein the absorber layer is deposited directly on the readout electronics in a low temperature process. The only FPD using a direct conversion mode and are commercially available for medical applications are in fact based on amorphous selenium (a-Se) absorbers. They offer large size and are relatively inexpensive to make (see for example S. Kasap et al. in Sensors 11, 5112 (2011), the entire disclosure of which is hereby incorporated by reference). The detective quantum efficiency achievable with polycrystalline and or amorphous semiconductors is, however, again rather low because of their poor electrical transport properties, making FPD derived from such materials ill-suited for interventional radiology.

By far the best direct X-ray imaging detectors for what concerns spatial, temporal and energy resolution as well as detective quantum efficiency are those based on single crystal absorbers. The list of materials suitable for the fabrication of single crystalline X-ray absorbers is rather limited because they need to have a suitable bandgap and must be of sufficient size and perfection. The list includes mainly silicon (Si), germanium (Ge), gallium arsenide (GaAs), cadmium telluride (CdTe) and cadmium zinc telluride (CdZnTe).

Semiconductor absorbers based on any of these materials offer spectral resolution, since the energy of an incident X-ray photon is proportional to the number of generated e-h pairs and thus measurable by a pulse height analysis in single-photon counting.

In Si, one needs on average 3.6 eV to create a single e-h pair (see for example R. C. Alig et al. in Phys. Rev. B 22, 5565 (1980); and R. C. Alig in Phys. Rev. B 27, 968 (1983), the entire disclosures of which are hereby incorporated by reference). On average this leads to 280 e-h pairs per keV of absorbed X-ray energy, from which it can be seen that the conversion efficiency exceeds that of a scintillator-photodiode combination by more than a factor of ten. On the other hand, its low atomic number Z, makes Si a poor absorber for photon energies above about 20 keV. Moreover, the Compton Effect competing with the photoelectric effect at high photon energies (>57 keV) tends to offset the energy resolution in photon-counting. According to recent studies, this problem can, however, be solved (see for example U.S. Pat. No. 8,378,310 to Bornefalk; and H. Bornefalk et al. in Phys. Med. Biol. 55, 1999 (2010), the entire disclosures of which are hereby incorporated by reference). Similarly, the problems of cross-talk between neighboring pixels and signal pileup for high count rates appear to be solvable (see for example U.S. Pat. No. 8,378,310 to Bornefalk; and Bornefalk et al. in Nucl. Instr. Meth. Phys. Res. A 621, 371 (2010), the entire disclosures of which are hereby incorporated by reference).

In the meantime, Si-strip detectors with energy discriminating capabilities have reached the commercial stage for breast imaging (see H.-M. Cho, Med Phys. 41 091903 (2014), the entire disclosure of which is hereby incorporated by reference). Segmented Si-strip detectors in edge-on geometry to cover most of the photon energy range used in computed tomography (CT) are under development (see for example X. Liu et al. in IEEE Trans. Nucl. Sci. 61, 1099 (2014), the entire disclosure of which is hereby incorporated by reference).

In the usual detector geometry, such as that of a FPD, the use of Si is limited to low photon energies because of its low Z. The only elemental semiconductor with a higher Z for which large wafers of excellent quality are commercially available is Ge. It has, however, the drawback of a small bandgap $E_g$ of only 0.66 eV, leading to a resistivity of only 50 Ωcm at room temperature, even when it is undoped and highly pure. As a result, Ge detectors need to be cooled, at least to about −50° C. in order to reduce the excessive dark current related to the low resistivity (see for example D. Pennicard et al. in Jinst 6, C11009 (2011), the entire disclosure of which is hereby incorporated by reference). Higher room temperature resistivities are offered by SiGe alloys up to the Ge content (around 80%) at which the nature of the bandgap changes from Si-like to Ge-like (see for example J. Weber et al. in Phys. Rev. B 40, 5683 (1989), the entire disclosure of which is hereby incorporated by reference). Since, however, large SiGe wafers are not commercially available, one has to resort to epitaxial growth on Si substrates in order to realize FPD based on SiGe. The large mismatch of lattice parameters and thermal expansion coefficients of Ge and Si cause, however, high defect densities (such as misfit and threading dislocations and stacking faults) and cracks in an epitaxial SiGe layer of sufficient thickness on the order of 100 µm or larger to serve as an X-ray absorber. In addition, device processing may not be permitted at all due to excessive wafer bowing resulting from the thermal misfit.

The problem of wafer bowing and layer cracking has been solved by a method involving deep Si-substrate patterning at a micron-scale, along with far-from-equilibrium epitaxial growth. This gives rise for example to space-filling, three-dimensional (3D) SiGe-crystals separated by tiny gaps (see for example International Patent Application No. WO 2011/135432 to H. von Känel; and C. V. Falub et al. in Science 335, 1330 (2012), the entire disclosures of which are hereby incorporated by reference). For sufficiently large aspect ratio of the crystals, provided that they exhibit faceted surfaces, the method leads furthermore to the expulsion of all threading dislocations, so that crystal regions at a distance of several microns from the interface are entirely defect-free (see for example C. V. Falub et al. in Sci. Rpts. 3, 2276 (2013), the entire disclosure of which is hereby incorporated by reference). The approach does not, however, eliminate the high density of misfit dislocations present at the SiGe/Si interface. In order to eliminate this deficiency, the Ge content in the 3D SiGe crystals must be slowly increased from zero up to some final value. This method of compositional grading has been used in the past to lower the threading dislocation density in epitaxial SiGe/Si films, but without affecting the misfit dislocation density (see for example E. A. Fitzgerald et al. in Appl. Phys. Lett. 59, 811 (1991), the entire disclosure of which is hereby incorporated by reference). In the tall 3D SiGe crystals suitable for X-ray absorbers, one can expect the misfit stress to be relaxed elastically provided that the grading rate is kept low enough. Because of the lack of misfit dislocations these structures should therefore be entirely defect-free (see for example M. Salvalaglio, J. Appl. Phys. 116, 104306 (2014), and F. Isa et al. in Acta Materialia 114, 97 (2016), the entire disclosures of which are hereby incorporated by reference).

While epitaxial SiGe absorbers can be grown on large wafers at least 200 mm in size, they are necessarily limited in thickness to a range of about 100-200 µm for example for cost reasons. Under these conditions, efficient X-ray absorption close to 100% is found only for tube voltages below about 35 keV. In medical applications such absorbers are therefore best suited for mammography.

Obviously, there is no such thickness limitation for bulk Ge wafers which for 1 mm and 2 mm absorb close to 100% of the radiation emitted by tubes operated at 40 keV and 50 keV, respectively. The X-ray absorption of GaAs is very similar to that of Ge because of similar Z, and large wafers are commercially available as well. The bandgap of GaAs is ~1.4 eV and it can be made semi-insulating with a resistivity up to 109 Ωcm, such that cooling is not necessary (see for example M. C. Veale et al. in Nucl Instr. Meth. Phys. Res. A 752, 6 (2014), the entire disclosure of which is hereby incorporated by reference). On the other hand the mobility-lifetime product is much inferior to that of elemental semiconductors such as Si and Ge, which negatively affects the charge collection efficiency and the energy resolution of detectors made from this material.

In order to compensate for the decreasing charge collection efficiency at large absorber thickness, a three-dimensional detector structure has therefore been conceived, in which electrodes are drilled into the absorber volume, permitting electron-hole pairs to be collected by lateral transport (see for example E. Gros d'Aillon et al. in Nucl. Instr. Meth. Phys. Res. A 727, 126 (2013), the entire disclosure of which is hereby incorporated by reference).

In principle, CdTe and CdZnTe with a Zn content of about 10% should be the best materials for efficient X-ray absorption, especially for the higher photon energies required for CT (up to about 140 keV), due to their even higher Z. These are II-VI semiconductors with a higher degree of iconicity than III-V semiconductors, such as GaAs mentioned above. They contain multiple deep trap levels which affect especially the hole transport, leading to the phenomenon of polarization in which positive charges pile up in front of the cathode under high X-ray flux levels (see for example D. S. Bale et al. in Phys. Rev. B 77, 035205 (2008), the entire disclosure of which is hereby incorporated by reference). This strongly modifies the electric field distribution inside the absorber and negatively affects the charge collection efficiency and the measured energy spectrum in the photon counting mode of the detector. Other effects degrading detector performance are pulse pileups (more severe compared to GaAs because of lower carrier mobility), charge sharing among neighboring pixels, fluorescence producing lower energy photons, and Compton scattering (see for example K. Taguchi et al. in Medical Physics 40, 100901 (2013), the entire disclosure of which is hereby incorporated by reference). Presently, perhaps the biggest disadvantage is, however, the lack of large high-quality wafers which makes these materials ill-suited for the fabrication of FPD and applications where a high-energy resolution is required.

Irrespective of the kind of material used for the X-ray absorber, the latter needs to communicate with the readout electronics by means of which the analog charge pulses generated by the absorbed photons can be amplified, shaped and transformed into digital signals. The fabrication of monolithic structures by direct deposition of the absorber onto the readout wafer, discussed above for polycrystalline and amorphous absorber materials, is not possible for single crystal absorbers because of the high thermal budget required by epitaxial (single crystalline) growth, the large lattice misfits causing high defect densities, and the thermal mismatch responsible for wafer bowing and layer cracking. Epitaxial SiGe absorbers grown in the form of tall crystals on patterned CMOS processed Si substrates may be the only exception offering sufficient material quality, but thermal budget constraints are present here as well and require a special high temperature metallization scheme for the read-out circuits, so that state-of-the-art CMOS processing cannot be used (see for example U.S. Pat. No. 8,237,126 to von Känel, the entire disclosure of which is hereby incorporated by reference).

The only monolithic pixel sensors with single crystal absorbers available to date are designed for particle detection in high-energy physics, where the Si absorption layer does not need to be thick (see for example S. Mattiazzo et al. in Nucl. Instr. Meth. Phys. Res. A 718, 288 (2013), the entire disclosure of which is hereby incorporated by reference).

In practice, establishing the electrical connections through which the charge pulses generated in the absorber by incident X-ray photons are transmitted to the readout unit requires some form of bonding process between the two. The common bonding technique for two-dimensional detectors used today is bump bonding, as for example employed by the Medipix collaboration, CERN (http://medipix.web.cern.ch) or by Dectris AG (http://www.dectris.ch, of Baden-Daettwil, Switzerland). This hybrid approach is very flexible, applicable in principle to any semiconductor material suitable for X-ray detection of which sufficiently large single crystals are available (see for example European Patent No. 0571135 to Collins et al., the entire disclosure of which is hereby incorporated by reference). Such bump-bonded detectors find numerous applications in biology (see for example E. Bertolucci in Nucl Sci. Meth. Phys. Res. A 422, 242 (1999), the entire disclosure of which is hereby incorporated by reference); material science (see for example R. Ballabriga et al. in Jinst 8, C02016 (2013), the entire disclosure of which is hereby incorporated by reference), including CT in material science (see for example S. Procz et al. in Jinst 8, C01025 (2013), the entire disclosure of which is hereby incorporated by reference). Very recently, a Medipix3RX spectroscopic pixel detector with a GaAs absorber has been introduced and shown to be suitable for spectroscopic CT acquisitions, and probably soon for small animal imaging (see for example E. Hamann et al. in IEEE Trans. Med. Imaging 34, 707 (2015), the entire disclosure of which is hereby incorporated by reference).

The bump bonding technique is, however, rather expensive and therefore ill-suited for the fabrication of large area detectors (FPD) such as the ones needed for example for Cone Beam Computed Tomography (CBCT). In order for the single readout chips to be buttable, the through-silicon-via (TSV) technology originally developed for the 3-dimensional integration of microelectronics chips must be used, adding to the complexity of bump bonding (see for example Z. Vykydal et al. in Nucl. Instr. Meth. in Phys. Res. A 591, 241 (2008) and D. Henry et al. in IEEE Electronic Components & Technology Conference 2013, pp. 568, the entire disclosures of which are hereby incorporated by reference). One way to overcome these limitations would be to replace the expensive bump bonding technique by direct wafer bonding, wherein the absorber wafer is bonded to the wafer containing the readout circuits. Detectors made by direct bonding of readout and absorber wafers can no longer be distinguished from those having epitaxial readout/absorber interfaces and therefore may be termed "monolithic" with equal justification as detectors featuring absorber layers directly grown onto the readout wafer. The fabrication of detectors by means of direct wafer bonding requires a low-temperature wafer bonding technique for which several approaches have become available only recently.

The first approach is based on hydrophobic bonding of two hydrogen passivated wafers. It has been shown to be applicable to the direct bonding of two Si wafers, each of which has been device processed prior to the bonding. Hydrophobic bonding has the advantage of providing electrically transparent interfaces because the native oxides have been removed by the H-passivating step. The interfacial hydrogen has to be removed after bonding, however, in order to result in high bond strength. This can be achieved by thermal annealing above the hydrogen desorption temperature, which is a critical step because of thermal budget constraints which do not allow temperatures above 450° C. for standard aluminum metallization. The annealing has the further disadvantage of gas evolution at the interface, gas bubbles causing electrically insulating voids. In order to remove such gas bubbles, trenches may be etched prior to the bonding (see for example U.S. Pat. No. 6,787,885 to Esser et al., the entire disclosure of which is hereby incorporated by reference). The main disadvantage of hydrophobic remains, i.e. the required removal of interfacial hydrogen by thermal annealing. In particular, this rules out the bonding of wafers differing in thermal expansion coefficients, such as for example bonding of Si to SiGe, GaAs or CdTe.

What is needed is therefore a low-temperature process resulting in electrically transparent direct wafer bonds of bulk strength without the need of any high temperature annealing step. Bulk bond strength has been achieved in a process of covalent wafer bonding developed for example by EV Group for Si-wafer bonding at temperatures below 100° C. or even as low as room temperature (see for example C. Flötgen et al. in ECS Transactions 64, 103 (2014), the entire disclosure of which is hereby incorporated by reference). Electrical transport experiments have shown, however, that the oxide removal by dry etching prior to covalent bonding may result in interfacial barriers hindering charge carriers to cross the bonding interface. Surface amorphization during oxide removal must therefore be avoided or amorphous layers be passivated for example by a hydrogen passivation step known in the art (see for example A. Loshachenko et al. in Phys. Stat. Sol. C 10, 36 (2013), and T. Jiang et al. in Phys. Stat. Sol. A 209, 990 (2012), the entire disclosures of which are hereby incorporated by reference).

This invention may be applied to the fabrication of large area monolithic pixel sensors even for high-Z absorber materials for which at present no large wafers can be manufactured at a bearable cost.

What is needed is Computed Tomography (CT) equipment which overcomes the excessive radiation exposure to which patients are subjected by present day FPD. Current energy integrating FPD are therefore to be replaced by FPD with energy discriminating capabilities, high sensitivity and superior spatial resolution. The use of the photon counting mode offers substantially lower radiation doses for a wide range of medical imaging procedures.

A CBCT unit may comprise at least one X-ray source and a FPD mounted on a gantry disk, allowing the patient to remain stationary during the examination (see for example R. Baba et al. in Comp. Med. Imaging and Graphics 26, 153 (2002), and R. Gupta et al. in Eur. Radiol. 16, 1191 (2006), the entire disclosures of which are hereby incorporated by reference). Alternatively, C-arm mounted CBCT units are ideally suited for imaging in the interventional suite (see for example S. Hirota et al. in Cardiovasc. Intervent. Radiol. 29, 1034 (2006), and R. C. Orth et al. in J. Vasc. Interv. Radiol. 19, 814 (2008), the entire disclosures of which are hereby incorporated by reference). C-arm mounted CBCT units employing such energy resolving digital FPD will allow real-time 2D tissue-specific imaging and volumetric data acquisition in a single rotation of the source and the FPD. The photon counting mode will permit the reduction of either the amount of contrast agent or the radiation dose while maintaining the contrast-to-noise ratio at the level of current FPD. As demonstrated by K. Taguchi et al. (in: Med Phys. October 2013, the entire disclosure of which is hereby incorporated by reference), the contrast dose may be reduced by e.g. 23% or the radiation dose by 41%. Si-based photon counting detectors can even contribute to an average dose reduction of approximately 40%, as demonstrated with the Philips MicroDose SI mammography system (Philips Healthcare, White paper, 2012. Comparison of Dose Levels in a National Mammography Screening Program).

SUMMARY OF THE INVENTION

The inventive structure of CBCT equipment includes a monolithic photon counting FPD for medical applications requiring real-time 3D imaging such as mammography, interventional guided procedures or external beam radiotherapy. The CBCT unit includes a monolithic FPD made from an X-ray absorber covalently bonded to a Si wafer containing the CMOS processed readout electronics. The electrical signals generated by radiation incident on the absorber are collected by implants in the CMOS wafer, and processed by the readout electronics.

It is the aim of the present invention to broaden the use of X-ray medical imaging through CBCT with new photon counting FPD facilitating many interventional guided procedures requiring 3D real-time imaging, like angiographic interventions or non-angiographic procedures such as mammography, image guided surgery in orthopedic, thoracic, abdominal, head and neck, and neuro surgery, biopsies, brachytherapy or external beam radiotherapy, percutaneous drain and stent placement or radiofrequency ablation.

It is an object of the invention to provide CBCT equipment allowing high resolution X-ray images with a high contrast-to-noise ratio suitable for soft-tissue differentiation.

It is a further object of the invention to provide CBCT equipment including monolithic FPD with energy discriminating capabilities suitable for high-energy X-ray imaging which is fabricated by bonding an X-ray absorber onto a CMOS processed wafer having the readout electronics.

It is another object of the invention to provide a CBCT with photon counting capability to reduce the radiation dose absorption during medical procedures.

BRIEF DESCRIPTION OF THE DRAWINGS

FIG. 10 shows information about 'Structure Code' and 'Detector Type'.

DETAILED DESCRIPTION OF THE PREFERRED EMBODIMENTS

It is the aim of this invention to enable a multitude of improved capabilities and new applications for X-ray 3D imaging for example in mammography and in the interventional suite at lower radiation dose by overcoming the limits of actual absorption materials in detectors and manufacturing processes.

Figure 1:
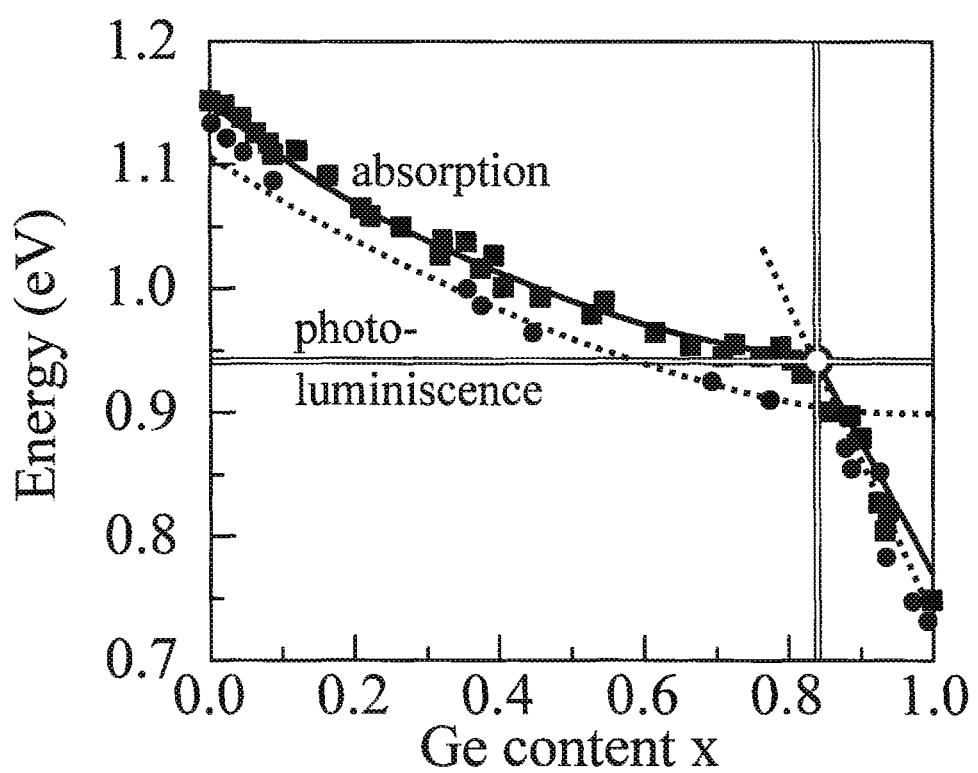
FIG. 1 is a graph showing the dependence of the band gap of Si1-xGex alloys as a function of the Ge content x.

The invention solves in particular the problems of materials incompatibility preventing the fabrication of sensitive, large area monolithic pixel detectors (FPD) employing high-Z materials to enhance absorption especially of X-ray photons with energies typically above 40 keV for use for example in C-arm Cone Beam Computed Tomography (CBCT) units. It is based on low-temperature direct wafer bonding techniques, preferably below 100° C. or even at room temperature, by means of which a CMOS processed readout unit and a single crystal absorber are combined in a monolithic detector structure. The invention is applicable in principle to any absorber material of which large wafers consisting of high quality single crystals are available or may become available in the future, such as for example GaAs, Ge, CdTe, $Cd_{1-x}Zn_xTe$ with x typically around 10% and SiGe. Alternatively, the invention is applicable to absorber materials which can be grown epitaxially on large Si wafers, provided they are substantially defect-free. One preferred class of materials identified to be suitable in particular for mammography applications are alloys with a Ge content x between about $0.2 \leq x \leq 0.8$ or even more preferably between about $0.6 \leq x \leq 0.8$. The band structure of $Si_{1-x}Ge_x$ alloys is Si-like with band gaps above 0.9 eV for $0 \leq x \leq 0.8$ according to FIG. 1 (see for example J. Weber et al. in Phys. Rev. B 40, 5683 (1989), the entire disclosure of which is hereby incorporated by reference). These band gaps are large compared to that of Ge amounting to 0.66 eV. The thermal generation of charge carriers will therefore be correspondingly lowered, resulting in a much higher resistivity and hence lower dark current of detectors based on such alloy absorbers. This in turn is expected to greatly relax the cooling requirements for these detectors.

Figure 2:
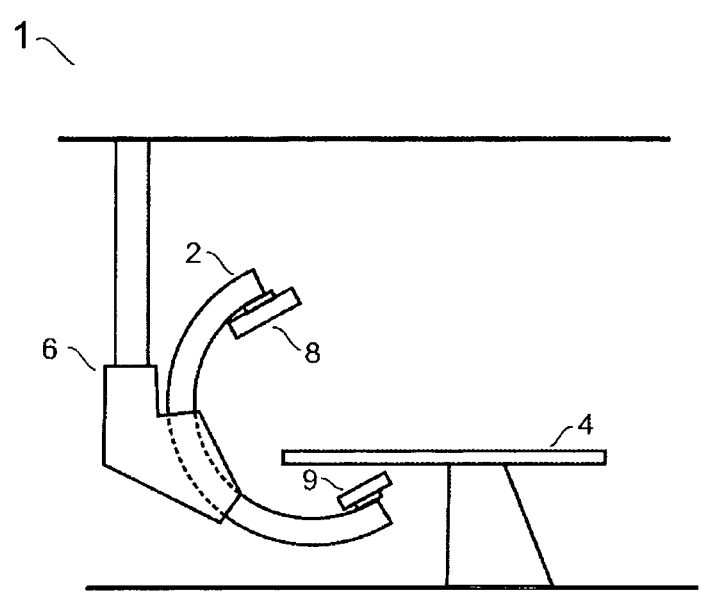
FIG. 2 is a schematic diagram of a C-arm cone-beam computed tomography unit.

Referring now to FIG. 2, a CBCT unit with energy integrating FPD based on indirect detection by scintillators and thin film photodiodes or on direct detectors having polycrystalline or amorphous absorber layers and thin film transistors known in the art is replaced with CBCT system 1 having FPD 8 equipped with a single crystal absorber communicating with a CMOS processed readout unit in which analog electrical signals generated by X-rays in the absorber are further amplified, shaped and transformed into digital signals. The readout unit has photon counting capability, enhancing the sensitivity for X-ray detection by approximately a factor of ten compared to polycrystalline or amorphous absorber systems. FPD 8 has a high spatial resolution up to about 100 μm or about 50 μm or even about 20 μm and is mounted on C-arm 2 along with at least one X-ray source 9. The readout unit communicates with one or more devices providing data collection, computation and/or storage functionality (e.g., a data collection device, a computation device and a storage device), disposed to receive electrical signals from the FPD and to generate computed tomography images on at least one computer screen.

Figure 3A:
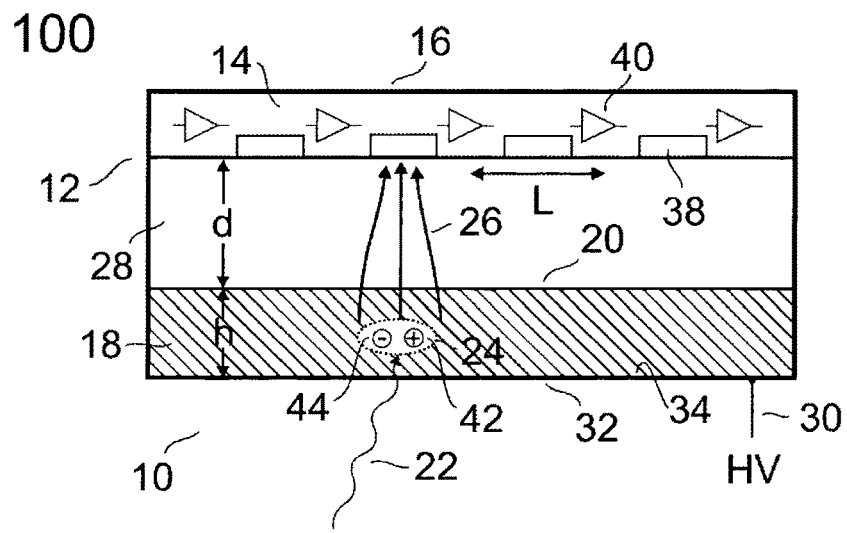
FIG. 3A is a cross-sectional view of a monolithic pixel detector with the absorber on the backside of the wafer and the CMOS processed readout unit on the front side.

Referring now to generic embodiment 100 of a FPD of FIG. 3A, the embodiment has a monolithic CMOS integrated pixel detector consisting of CMOS processed chip 12 with readout unit 14 on the front side 16 and absorber 18 attached by direct wafer bonding on the back side 20. CMOS processed chip 12 is preferably a Si chip as known in the art. X-rays 22 incident on absorber 18 may create electron-hole pairs 24 which may be pulled apart, the individual charges drifting towards the front side 16 of chip 12 and the surface 34 of absorber 18, respectively, when an electric field represented by electric field lines 26 is present in absorber 18 of thickness h and in drift region 28 of Si chip 12 of thickness d. One preferred way of establishing this electric field is to use very low doping giving a first conductivity type to chip 12 (for example n-doping). Preferably, the low doping of chip 12 results in a high resistivity of 0.5-2 kΩcm or 2-5 kΩcm or even 5-20 kΩcm. Similarly, absorber wafer 18 is preferably undoped or low doped as well, and exhibits a conductivity of opposite type to that of chip 12 (for example p-doping). Absorber wafer 18 need not be actively doped at all as long as its conductivity type is opposite to that of chip 12. Chip 12 and absorber 18 therefore form a heterojunction p-n diode characterized by the presence of a large electric field in the space charge region when the diode is reverse biased by applying voltage 30 of the appropriate sign.

Depending on the doping sequence and the sign of the voltage 30 applied to the metallized back contact 32 of absorber 18, either holes 42 or electrons 44 may drift along the electric field lines 26 towards the front side 16 of chip 12 to be collected by implants 38 defining the pixels of the detector of size L. The pixel size L may be in the range of about 5-200 μm, or preferably in the range of about 10-100 μm, or even more preferably in the range of about 20-50 μm. The electrical signals induced by the charges 42 or 44 collected by implants 38 may subsequently be processed by circuits 40 of readout unit 14. It is advisable to keep the thickness d of drift region 28 low in order to limit voltage 30 required for its depletion. Preferably the thickness d is in the range of 10-200 µm or even more preferably about 10-50 µm. The optimum thickness h of absorber 18 depends on the absorber material and the energies of the particles to be detected. It may range from about 20 µm to 200 µm or from 200 µm to 1 mm or even to several mm. For example for mammography applications a 100-200 µm thick Ge-rich $Si_{1-x}Ge_x$ absorber may be sufficient. For applications requiring X-ray energies substantially above 30 keV thicker absorbers must be used and/or absorbers from materials with higher Z. Fully CMOS processed chip 12, including all metallization layers, may for example have a size of about 2×2 $cm^2$ or larger such as 4×4 $cm^2$ or 6×6 $cm^2$ or 10×10 $cm^2$ or even 15×15 $cm^2$ or yet more, depending on the available size of absorber 18. In the limiting case, chip 12 may for example cover a substantial part of a complete 200 mm wafer or even a 300 mm wafer.

Figure 3B:
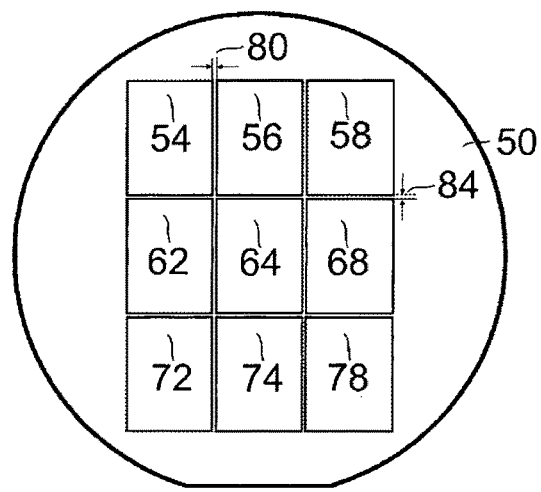
FIG. 3B is a top view of 9 buttable pixel detector tiles making up part of a FPD.

Referring now to FIG. 3B, a major advantage of the direct wafer bonding approach of the invention is that, for example, readout chips 54-78 are buttable, preferably on four sides, with minimal dead space 80, 84 between the tiles. Spacings 80, 84 may, for example, be smaller than 100 µm or even smaller than 50 µm. In the example of FIG. 3B CMOS processed readout chips are direct-wafer-bonded to absorber wafer 50 which may for example be as large as 200 mm or even 300 mm. Note that many more tiles than shown in FIG. 3B may be bonded to absorber wafer 50. In principle, the whole CMOS processed readout wafer may be bonded to absorber 50. Alternatively, when absorber areas are of smaller size, for example of the size of single readout chips, the absorber pieces may be bonded to the readout wafer by direct wafer bonding. Much larger than wafer scale FPD can be made for example by tiling several of the structures of FIG. 3B. In this way, FPD with a size for example of 20×20 $cm^2$ or even larger, for example about 40×40 $cm^2$, can be made.

Figure 3C:
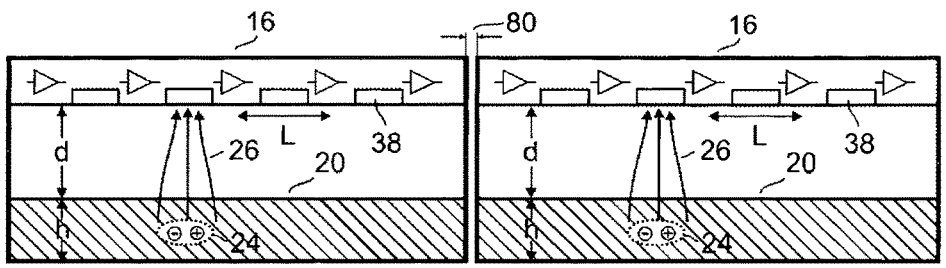
FIG. 3C is a cross-sectional view of two buttable pixel detector tiles making up part of a FPD.

Referring now to FIG. 3C, another major advantage of the direct wafer bonding approach of the invention is that electrical contacts to the readout wafer do not require the fabrication of TSV. In fact, all electrical contacts, with the possible exception of guard ring contacts in the case of small absorber areas, can be made on the front side 16 of readout chips 12. This is a big difference compared with the approach of bump bonded pixel detectors, wherein the absorber covers the upper side 16 of readout chips 12, such that TSV are needed to contact the chips electrically. Especially for absorber materials for which no large wafers are available, it may be advantageous to implant guard rings around the periphery of the tiles prior to direct wafer bonding. In this case, the guard rings are preferably contacted by TSV. Alternatively, the guard rings may be foreseen on the readout chip itself, in which case no TSV are needed at all.

Figure 4A:
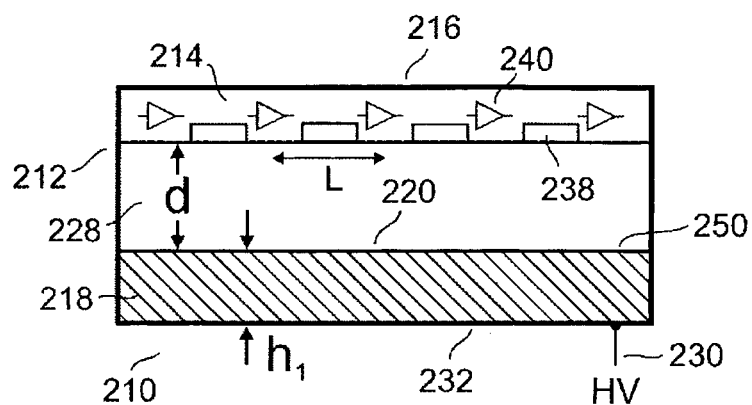
FIG. 4A is a cross-sectional view of a monolithic pixel detector with a bonded absorber crystal on the back of a CMOS processed readout unit.

Referring now to FIG. 4A, the first embodiment 200 of monolithically integrated pixel detector 210 is made up of a CMOS processed wafer 212 with readout unit 214 on the front side 216 and absorber 218 on the back side 220. Embodiment 200 may be suitable especially for absorber layers 218, the thermal expansion coefficients of which do not deviate strongly from that of Si, such as for example SiC. It may also be applicable to absorber layers 218 which are thermally mismatched with Si, such as for example GaAs, Ge, CdTe and CdZnTe as long as the operating temperature of detector 210 does not deviate much from room temperature. A temperature rise to 50° C. or even 100° C. may still be considered to be permissible. Single crystalline absorber layer 218 is bonded by direct wafer bond 250 at or near room temperature to the backside 220 of CMOS processed wafer 212. Direct wafer bond 250 is preferably a covalent bond, providing an intimate electrical contact, preferably with few or no interface states or interface states passivated for example by hydrogen to improve interfacial charge transport (i.e. to attain ohmic behavior), between absorber layer 218 and drift region 228 across the entire backside 220 of wafer 212. In order for an intimate electrical contact to be established the backside of wafer 212 and the bonding surface of absorber layer 218 have to be atomically flat and particle-free as well as oxide-free. It may be advisable to subject the backside 220 of wafer 212 and the bonding surface of absorber layer 218 to a chemical-mechanical polishing step prior to the surface treatment required for oxide-free covalent bonding. The bonding process may comprise steps of optional pre-bonding annealing of the as yet oxidized surfaces to reduced moisture and optional mild post-bonding annealing. Pre- and post-bonding annealing are carried out at low temperature. Annealing temperatures may range between 100° C. and 200° C., or between 200° C. and 300° C., or between 300° C. and 400° C. In any case they must be below about 450° C. in order to avoid disintegration of the metallization of CMOS processed wafer 212.

When a large voltage 230 is applied to metallized back contact 232 of the absorber, resulting substantially in the depletion of absorber 218 and drift region 228 of CMOS processed wafer 212, e-h pairs generated by absorbed high energy material particles or photons are separated in the associated electric field and collected by implants 238, defining the pixel size, and metal electrode 232, respectively.

Figure 4B:
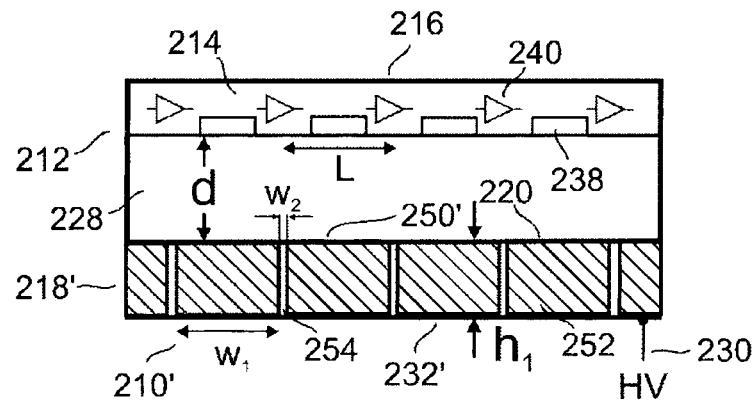
FIG. 4B is a cross-sectional view of a monolithic pixel detector with a pixelated absorber crystal bonded to the back of a CMOS processed readout unit.

Referring now to FIG. 4B, the second embodiment 200' of monolithically integrated pixel detector 210' is made up of CMOS processed wafer 212 with readout unit 214 on the front side 216 and absorber 218' on the back side 220. Embodiment 200' may be of suitable especially for absorber layers 218' which are lattice matched but thermally mismatched with Si, such as for example GaP. It may be applicable also to absorber layers 218' which are thermally and lattice mismatched with Si, such as for example GaAs, Ge, CdTe, CdZnTe and SiC. Absorber layer 218' is pixelated, i.e. it is made up of distinct absorber patches 252 of width $w_1$, separated by trenches 254 of width $w_2$. The width $w_1$ of distinct absorber patches 252 may be larger, equal or smaller than the pixel size L defined by implants 238. The width $w_2$ of trenches 254 is preferably smaller than the width $w_1$ of distinct absorber patches 252 or even more preferably much smaller. The width $w_2$ of trenches 254 may be as narrow as the minimum width achievable by the lithography and deep reactive ion etching techniques known in the art (see for example X. Li et al., in Sensors and Actuators A87, 139 (2001) and E. H. Klaassen, in Sensors and Actuators A52, 132 (1996), the entire disclosure of which are hereby incorporated by reference). Preferably backside 220 of CMOS processed wafer 212 and absorber patches 252 are bonded by covalent bonds 250' providing an intimate electrical contact, preferably with few or no interface states or interface states passivated for example by hydrogen to improve interfacial charge transport (i.e. to attain ohmic behavior), between absorber layer 218' and drift region 228 across the entire backside 220 of wafer 212. In order for an intimate electrical contact to be established the backside of wafer 212 and the bonding surface of absorber layer 218' have to be atomically flat and particle-free as well as oxide-free. It may be advisable to subject backside 220 of wafer 212 and the bonding surface of absorber layer 218' to a chemical-mechanical polishing step prior to the surface treatment required for oxide-free covalent bonding. The bonding process preferably includes steps of optional pre-bonding annealing to reduced moisture on the as yet oxidized surfaces and post-bonding annealing. Patterning of absorber 218' into absorber patches 252 is preferably carried out after the optional low temperature pre-bonding anneal in order to avoid stress exerted during the optional higher temperature post-bonding anneal because of different thermal expansion coefficients of wafer 212 and absorber layer 218'. Pre- and post-bonding annealing are carried out at low temperature. Annealing temperatures may range between 100° C. and 200° C., or between 200° C. and 300° C., or between 300° C. and 400° C. In any case they must be below about 450° C. in order to avoid disintegration of the metallization of CMOS processed wafer 212. Distinct absorber patches 252 may be electrically connected by metallized back contact 232' extending substantially across the whole surface of the absorber.

When a large voltage 230 is applied to metallized back contact 232' of absorber 218', resulting substantially in the depletion of absorber 218' and drift region 228 of CMOS processed wafer 212, e-h pairs generated by absorbed high energy material particles or photons are separated in the associated electric field and collected by implants 238, defining the pixel size L, and metal electrode 232', respectively.

Figure 4C:
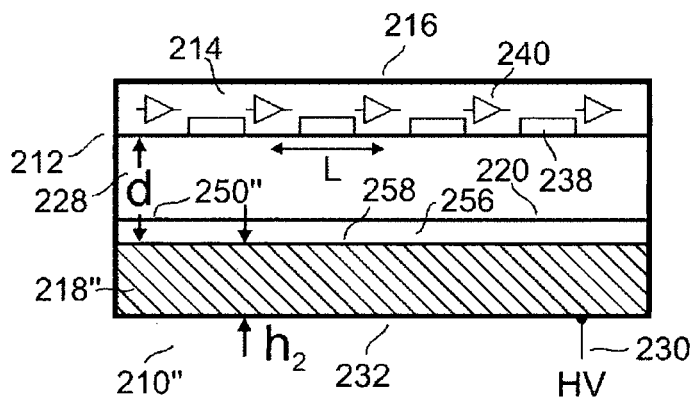
FIG. 4C is a cross-sectional view of a monolithic pixel detector with a substrate with an epitaxial absorber layer bonded to the back of a CMOS processed readout unit.

Referring now to FIG. 4C, the third embodiment 200'' of monolithically integrated pixel detector 210'' is made up of CMOS processed wafer 212 with readout unit 214 on the front side 216 and absorber 218'' on the back side 220. Embodiment 200'' is most suitable especially for absorber layers 218'' which cannot be grown in the form of large single crystals suitable for wafer fabrication, but which can be grown in the form of epitaxial layers on a large Si substrate 256. Absorber layer 218'' is preferably made from a semiconductor material which is substantially lattice matched to the Si substrate, such as for example GaP, in order to avoid a high density of misfit dislocations to be present at interface 258 between substrate and epitaxial layer. It may also comprise compositionally graded layers, where the layers closest to the interface with the Si substrate are lattice matched, such as $GaP_{1-x}As_x$ with x ranging from 0 to 1 within a thickness of several μm, after which the full lattice mismatch of about 4% characteristic of pure GaAs is reached. Depending on the grading rate, i.e., the rate at which the composition x is changed as a function of layer thickness, dislocations are distributed over a smaller or larger volume of the graded layer. The smaller the grading rate, the lower the density of misfit dislocations per volume fraction of the layer. The density of threading dislocations extending to the growth front of the graded layer is correspondingly reduced with decreasing grading rate.

In embodiment 200'', direct wafer bond 250'' is a covalent Si—Si bond between back side 220 of CMOS processed wafer 212 and substrate 256 on which absorber 218'' is epitaxially grown. In order for an intimate electrical contact to be established, the backside of wafer 212 and the bonding surface of substrate 256 have to be atomically flat and particle-free as well as oxide-free. It may be advisable to subject the backside 220 of wafer 212 and the bonding surface of substrate 256 to a chemical-mechanical polishing step prior to the surface treatment required for oxide-free covalent bonding. The bonding process preferably includes steps of optional pre-bonding annealing to reduce moisture on the as yet oxidized surfaces and post-bonding annealing. Pre- and post-bonding annealing are carried out at low temperature. Annealing temperatures may range between 100° C. and 200° C., or between 200° C. and 300° C., or between 300° C. and 400° C. In any case they must be below about 450° C. in order to avoid disintegration of the metallization of CMOS processed wafer 212.

When a large voltage 230 is applied to metallized back contact 232 of the absorber, resulting substantially in the depletion of absorber 218'' and drift region 228 of CMOS processed wafer 212, e-h pairs generated by absorbed high energy material particles or photons are separated in the associated electric field and collected by implants 238, defining the pixel size L, and metal electrode 232, respectively.

Figure 4D:
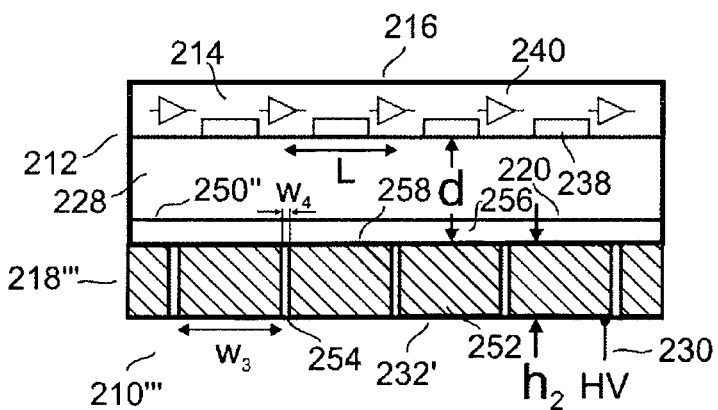
FIG. 4D is a cross-sectional view of a monolithic pixel detector with a substrate with a pixelated epitaxial absorber layer bonded to the back of a CMOS processed readout unit.
Figure 5A:
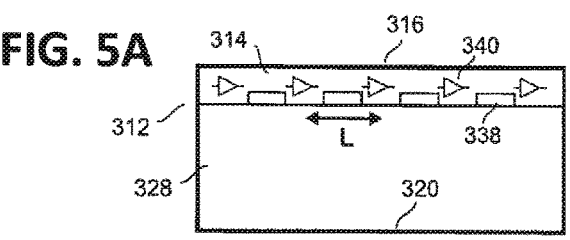
FIG. 5A is a cross-sectional view of a CMOS processed wafer with a readout unit.
Figure 5B:
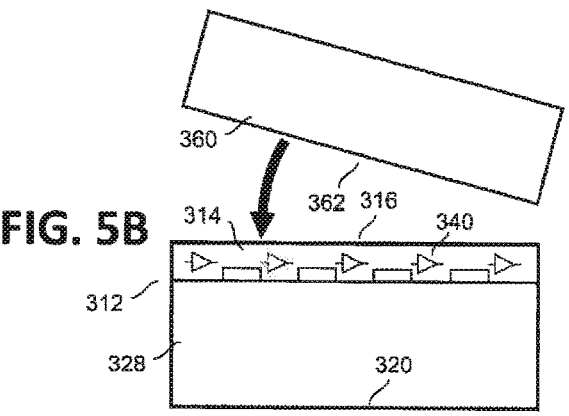
FIG. 5B is a cross-sectional view of a CMOS processed wafer with a readout unit and a handling wafer.
Figure 5C:
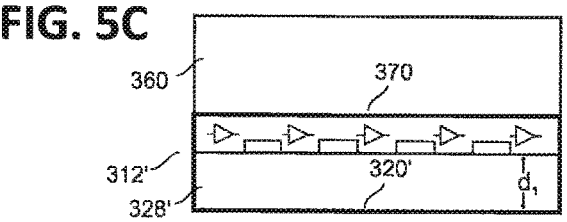
FIG. 5C is a cross-sectional view of a thinned CMOS processed wafer bonded to a handling wafer.
Figure 5D:
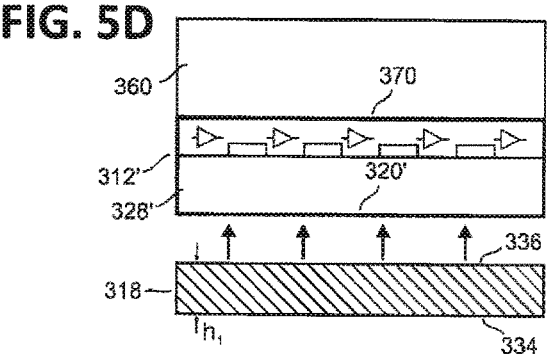
FIG. 5D is a cross-sectional view of a thinned CMOS processed wafer with a readout unit and an absorber layer.
Figure 5E:
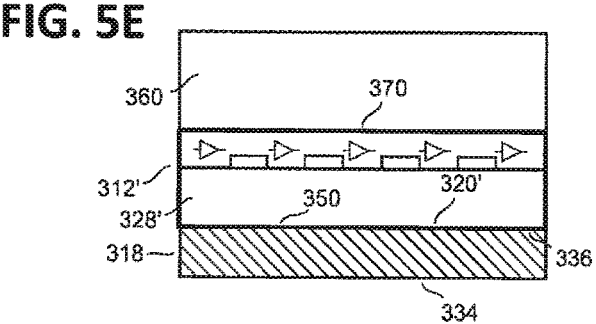
FIG. 5E is a cross-sectional view of a thinned CMOS processed wafer with a readout unit and a handling wafer bonded to the front, and an absorber layer bonded to the back.
Figure 5F:
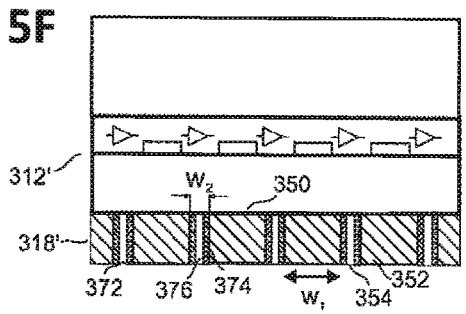
FIG. 5F is a cross-sectional view of a thinned CMOS processed wafer with a readout unit, a handling wafer bonded to the front, and a pixelated and passivated absorber layer bonded to the back.
Figure 5G:
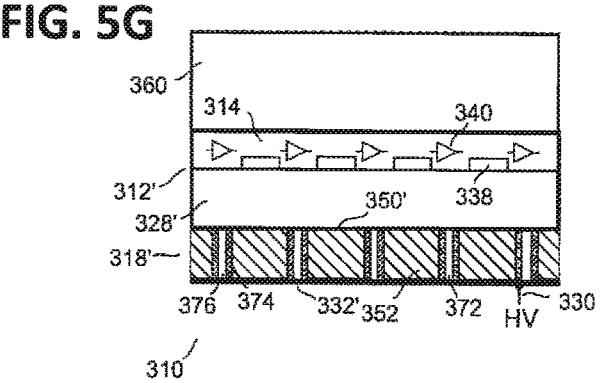
FIG. 5G is a cross-sectional view of a thinned CMOS processed wafer with a readout unit, a handling wafer bonded to the front, and a pixelated, passivated and contacted absorber layer bonded to the back.

Referring now to FIG. 4D, the fourth embodiment 200''' of monolithically integrated pixel detector 210' is made up of CMOS processed wafer 212 with readout unit 214 on the front side 216 and pixelated absorber 218''' on the back side 220. Embodiment 200''' is the preferred embodiment for absorber layers 218''' which cannot be grown in the form of large single crystals suitable for wafer fabrication, but which can be grown in the form of epitaxial patches of width $w_3$ separated by trenches 254 of width $w_4$ on a large Si substrate 256. The width $w_3$ of distinct absorber patches 252 may be larger, equal or smaller than the pixel size L defined by implants 238. The width $w_4$ of trenches 254 are preferably smaller that the width $w_3$ of absorber patches 252 and even more preferably much smaller. For absorber patches 252 defined by the spacing of dielectric mask openings in ART, they may be as narrow as the minimum width achievable by the lithography and deep reactive ion etching techniques, for example 1-5 μm. The width $w_4$ of trenches obtained by self-limited lateral growth of absorber patches 252 may be even smaller, for example 100 nm-1 μm, or even 20 nm-100 nm.

Embodiment 200''' is the most preferred embodiment for absorber layers which are both lattice and thermally mismatched with the Si substrate 256. The most preferred material of absorber layers 218''' may be a alloy which may preferably have a Ge content above 20%. In a preferred aspect of the embodiment the $Si_{1-x}Ge_x$ alloy may have a high Ge content x of about $0.6 \leq x \leq 0.8$. When having such SiGe alloy absorbers with a thickness of about 100-200 μm, embodiment 200''' is especially well suited for applications limited to X-ray energies below 40 keV, such as mammography applications. In an even more preferred aspect of the embodiment, the $Si_{1-x}Ge_x$ alloy may be compositionally graded to a high Ge content x of about $0.6 \leq x \leq 0.8$ and optionally have a cap region of constant composition substantially equal to the final composition of the graded part, which may for example be graded linearly. In a most preferred aspect of embodiment 200''' interface 258 between Si substrate 256 and pixelated absorber 218''' is substantially defect-free. This can be achieved for example by choosing width $w_3$ of semiconductor patches 252 forming pixelated absorber 218''' and the grading rate both sufficiently small to permit elastic relaxation of the misfit stress during the epitaxial growth of absorber 218''' (see for example M. Salvalaglio et al. in J. Appl. Phys. 116, 104306 (2014), and F. Isa et al. in Acta Materialia 114, 97 (2016), the entire disclosures of which are hereby incorporated by reference). The grading rate may preferably be chosen below about 3%, or below about 2%, or even below 1%. In other aspects of the embodiment interface areas 258 between substrate 256 and patches 252 of pixelated absorber 218''' may not be substantially defect-free, but of sufficiently small size to keep dark currents at acceptable levels, when a large voltage 230 is applied to metallized back contact 232' of absorber 218''' and implants 238 of CMOS processed wafer 212. As known to one skilled in the art, such small interface regions are commonly employed for example in techniques of aspect ratio trapping (ART), wherein threading dislocations are trapped at the sidewalls of windows in a dielectric mask into which a semiconductor is selectively grown (see for example I. Åberg et al., IEDM San Francisco, 2010, the entire disclosure of which is hereby incorporated by reference). With the help of ART, in addition, other absorber materials may be used apart from SiGe, such as GaAs, CdTe or CdZnTe.

The width $w_4$ of trenches 254 is preferably smaller (ratio of about 1:2_) than the size $w_3$ of absorber patches 252 or even more preferably much smaller (ratio of about 1_:10 or even 1:100). The width $w_1$ of trenches may be below 1 µm or below 200 nm or even below 100 nm, when a self-limited epitaxial growth process and deeply patterned substrates are used to define the size $w_3$ of absorber patches 252 (see for example International Patent Application No. WO 2011/135432 to von Känel, the entire disclosure of which is hereby incorporated by reference). Alternatively, when a method of ART is used to define the size $w_3$ of absorber patches 252, the width $w_4$ of trenches 254 may be defined by the spacing of dielectric windows, which may be as narrow as the minimum width achievable by the lithography and deep reactive ion etching techniques used for patterning the dielectric mask. Preferably backside 220 of CMOS processed wafer 212 and substrate 256 are bonded by covalent bonds 250'' providing an intimate electrical contact, preferably with few or no interface states or interface states passivated for example by hydrogen to improve interfacial charge transport (i.e. to attain ohmic behavior), between absorber layer 218' and drift region 228 across the entire backside 220 of wafer 212. In order for an intimate electrical contact to be established, backside 220 of wafer 212 and the bonding surface of substrate 256 also have to be atomically flat and particle-free as well as oxide-free. It may be advisable to subject backside 220 of wafer 212 and the bonding surface of absorber layer 256 to a chemical-mechanical polishing step prior to the surface treatment required for oxide-free covalent bonding. The bonding process preferably includes steps of optional pre-bonding annealing to reduced moisture on the as yet oxidized surfaces and optional post-bonding annealing. Pre- and post-bonding annealing steps are carried out at low temperature. Annealing temperatures may range between 100° C. and 200° C., or between 200° C. and 300° C., or between 300° C. and 400° C. In any case they must be below about 450° C. in order to avoid disintegration of the metallization of CMOS processed wafer 212. Distinct absorber patches 252 may be electrically connected by metallized back contact 232' extending substantially across the whole surface of the absorber.

When a large voltage 230 is applied to metallized back contact 232' of absorber 218''', resulting substantially in the depletion of absorber 218''' and drift region 228 of CMOS processed wafer 212, e-h pairs generated by absorbed high energy material particles or photons are separated in the associated electric field and collected by implants 238, defining the pixel size L, and metal electrode 232', respectively.

Referring now to FIGS. 5A-5G, fabrication 300 of monolithic pixel detector 310 may include the following steps. In a first step (FIG. 5A) Si wafer 312 which may be lightly n-doped or lightly p-doped with a resistivity preferably above 500 Ωcm is CMOS processed to obtain readout electronics 314, the part 340 of which may be contained in every pixel of size L, defined by the spacing of charge collection implants 338. In a second step (FIG. 5B), handling wafer 360 may be bonded onto the optionally chemically-mechanically polished surface 316 of wafer 312. The bond 370 between surface 316 of CMOS wafer 312 and surface 362 of handling wafer 360 may not be a permanent bond, but must be strong enough to permit thinning of the CMOS wafer in a third step (FIG. 5C) for example in a chemical-mechanical polishing step to reduce the thickness $d_1$ of lightly doped region 328' to below 200 µm. In a preferred aspect of the embodiment, the thickness $d_1$ is below 100 µm, and in an even more preferred aspect it may be as low as for example 10-20 µm. In a fourth step (FIG. 5D) surface 320' of thinned CMOS wafer 312 and upper surface 336 of absorber wafer 318 (having lower surface 334) of thickness $d_2$, which may also have undergone chemical-mechanical polishing and an optional shallow hydrogen implant, may be prepared for oxide-free covalent bonding for example by sputter etching the surface oxide in a neutralized plasma as known in the art (see for example C. Flötgen in ECS Trans. 64, 103 (2014), the entire disclosure of which is hereby incorporated by reference). An optional pre-bonding anneal and optional post-bonding anneal at low temperature in a fifth step (FIG. 5E), preferably in the range between about 100° C. and 200° C., or between 200° C. and 300° C., or between 300° C. and 400° C., provides strong and electrically conductive bond 350 between backside 320' of CMOS processed and thinned wafer 312' and surface 336 of absorber wafer 318. The optional post-bonding anneal may help in eliminating any interfacial barriers blocking electrical charge transport across the bonding interface, for example by causing optionally implanted hydrogen to passivate the dangling bonds so that ohmic behavior is attained.

If the absorber material is characterized by a large mismatch of the thermal expansion coefficients with respect to those of Si wafer 312', absorber wafer 318' is preferably patterned in the form of distinct patches 352 of width $w_1$ separated by trenches 354 of width $w_2$ in a sixth step (FIG. 5F) before the post-bonding anneal in order to avoid any undesirable thermal stress. The width $w_1$ of distinct absorber patches 352 may be larger, equal or smaller than the pixel size L defined by implants 338. The width $w_2$ of trenches 354 is preferably smaller than the size WI of absorber patches 352 or even more preferably much smaller. The width $w_2$ of trenches 354 may be as narrow as the minimum width achievable by the lithography and deep reactive ion etching techniques known in the art (see for example X. Li et al., in Sensors and Actuators A87, 139 (2001) and E. H. Klaassen, in Sensors and Actuators A52, 132 (1996), the entire disclosure of which are hereby incorporated by reference). It may be advisable to coat sidewalls 374 of distinct absorber patches 352 with a dielectric film 376 providing a surface passivation and thereby reducing leakage currents during the operation of the pixel sensor. In a seventh step (FIG. 5G) trenches 354 may be optionally filled with insulating material 372, and metallic contact 332' may be formed preferably as a continuous metallization layer connecting distinct absorber patches 352 in parallel.

When a large voltage 330 is applied to metallized back contact 332' of absorber 318', resulting substantially in the depletion of absorber 318' and drift region 328' of thinned CMOS processed wafer 312', e-h pairs generated by absorbed high energy material particles or photons are separated in the associated electric field and collected by implants 338 of pixel detector 310.

Referring now to FIGS. 6A-6K, fabrication 400 of monolithic pixel detector 410, may include the following steps, although not necessarily executed in the order shown. In a first step (FIG. 6A), Si wafer 412 with front side 416 and backside 420, which may for example be lightly n-doped or lightly p-doped with a resistivity preferably above 500 Ωcm, is CMOS processed to obtain readout electronics 414 part 440 of which may be contained in every pixel of size L, defined by the spacing of charge collection implants 438. In a second step (FIG. 6B), Si wafer 456 may be patterned and cleaned in order to serve as a substrate for absorber 418 to be epitaxially grown in the form of distinct patches 452 of width $w_3$ and height $h_2$ separated by trenches 454 of width $w_4$. The width $w_3$ of distinct absorber patches 452 may be larger, equal or smaller than the pixel size L defined by implants 438. The width $w_4$ of trenches may be below 1 μm or below 200 nm or even below 100 μm, when a self-limited epitaxial growth process and deeply patterned substrates are used to define the size $w_3$ of absorber patches 452 as known in the art (see for example International Patent Application No. WO 2011/135432 to von Känel, the entire disclosure of which is hereby incorporated by reference). Alternatively, when a method of ART is used to define the size $w_3$ of absorber patches 452, the width of trenches $w_4$ may be defined by the spacing of dielectric windows, which may be as narrow as the minimum width achievable by the lithography and deep reactive ion etching techniques known in the art (see for example X. Li et al., in Sensors and Actuators A87, 139 (2001) and E. H. Klaassen, in Sensors and Actuators A52, 132 (1996), the entire disclosure of which are hereby incorporated by reference). After the epitaxial growth, sidewalls 474 of distinct patches 452 may optionally be passivated by a dielectric passivation layer. The passivation layer may comprise for example first dielectric layer 436 designed to control surface leakage along sidewalls 474 when pixel detector 410 is in operation. First dielectric layer may be a thermal oxide or an oxide formed by atomic layer deposition (ALD). The passivation layer may optionally comprise second dielectric layer 476, which may provide additional protection of sidewalls 474 against environmental influences. It may for example be made of $Al_2O_3$ which may be deposited by atomic layer deposition as known in the art. Trenches 454 may additionally be filled by dielectric filling material 472 to provide stability in an optional step of chemical mechanical polishing as a preparation of absorber surface 434 for a subsequent wafer bonding step.

Figure 6A:
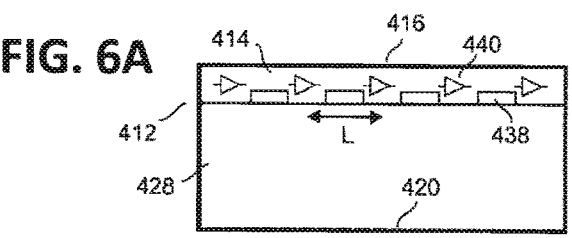
FIG. 6A is a cross-sectional view of a CMOS processed wafer with a readout unit.
Figure 6B:
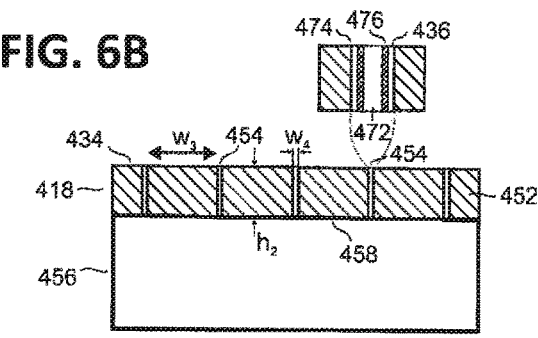
FIG. 6B is a cross-sectional view of a wafer with a pixelated and passivated epitaxial absorber layer.
Figure 6C:
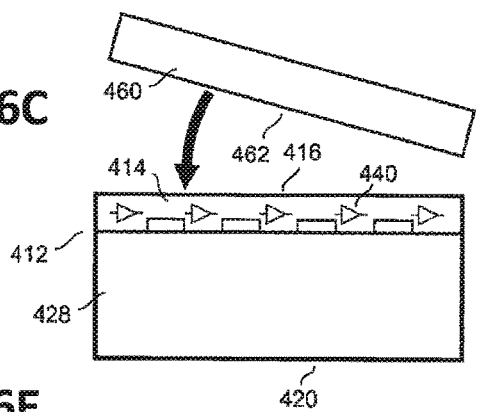
FIG. 6C is a cross-sectional view of a CMOS processed wafer with a readout unit and a handling wafer.
Figure 6D:
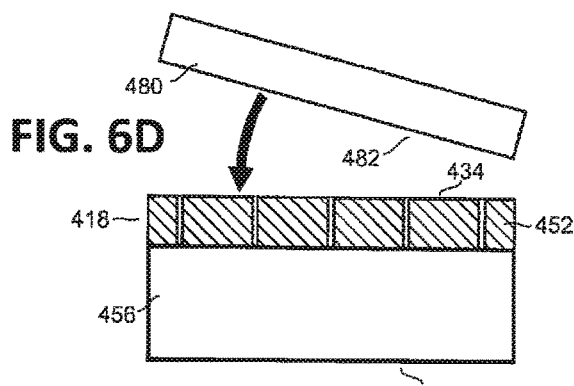
FIG. 6D is a cross-sectional view of a wafer with a pixelated and passivated epitaxial absorber layer and a handling wafer.
Figure 6E:
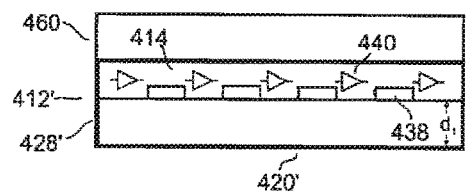
FIG. 6E is a cross-sectional view of a thinned CMOS processed wafer bonded to a handling wafer.
Figure 6F:
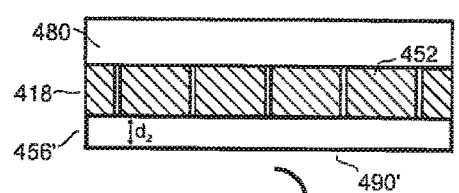
FIG. 6F is a cross-sectional view of a thinned substrate with a pixelated epitaxial absorber layer bonded to a handling wafer.
Figure 6H:
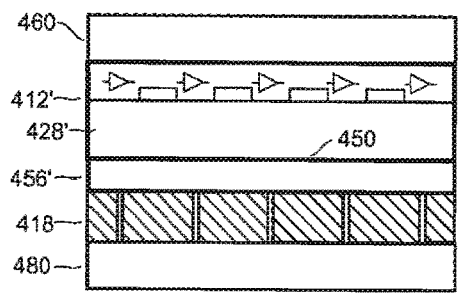
FIG. 6H is a cross-sectional view of a thinned CMOS processed wafer bonded to a thinned substrate with a pixelated epitaxial absorber layer.
Figure 6G:
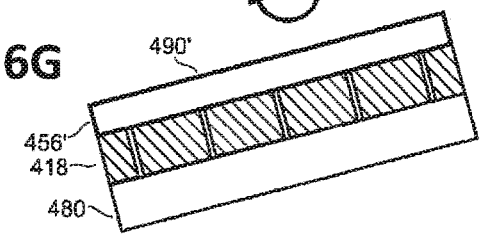
FIG. 6G is a cross-sectional view of a flipped over thinned substrate with a pixelated epitaxial absorber layer bonded to a handling wafer.
Figure 6I:
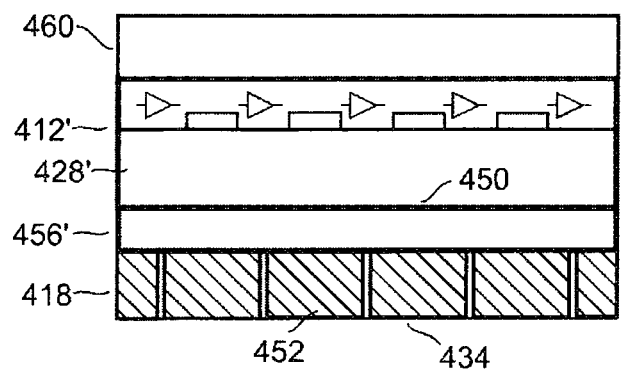
FIG. 6I is a cross-sectional view of a thinned CMOS processed wafer bonded to a thinned wafer with a pixelated epitaxial absorber layer after removal of the handling wafer.
Figure 6J:
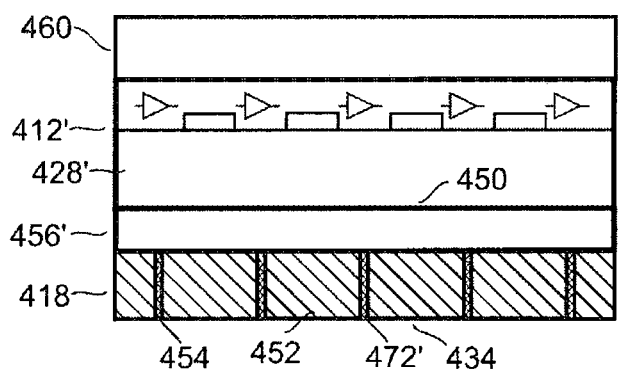
FIG. 6J is a cross-sectional view of a thinned CMOS processed wafer bonded to a thinned wafer with a pixelated epitaxial absorber layer after removal of handling wafer and bonding residues.
Figure 6K:
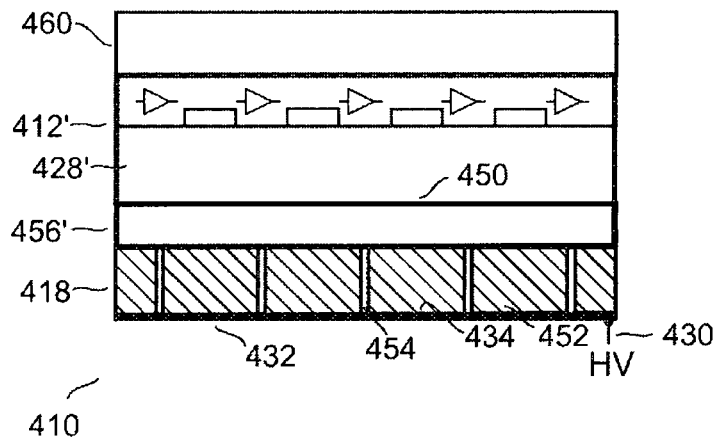
FIG. 6K is a cross-sectional view of a thinned CMOS processed wafer bonded to a thinned wafer with a pixelated, electrically contacted epitaxial absorber layer.

Referring to FIG. 6C, in third step, surface 416 of Si wafer 412 may undergo an optional chemical mechanical polishing step before being bonded to surface 462 of handling wafer 460 as a means to provide mechanical stability in the subsequent thinning of drift region 428 for example in a chemical mechanical polishing step. Referring to FIG. 6D, in a fourth similar step, surface 434 of epitaxial absorber 418 may be bonded to surface 482 of handling wafer 480 as a means to provide mechanical stability in the subsequent thinning of substrate 456 for example in a chemical mechanical polishing step. Referring now to FIG. 6E, in the fifth step, drift region 428 of CMOS processed wafer 412 is thinned for example in a plasma etching or chemical mechanical polishing step. Thinned wafer 412' with drift region 428' has a thickness $d_1$ which is preferably between about 10-100 μm, and even more preferably between about 10-20 μm. Referring now to FIG. 6F, in a sixth step, substrate 456 is thinned for example in a plasma etching or chemical mechanical polishing step. Thinned substrate 456' has a thickness $d_2$ which is preferably between about 10-100 μm, and even more preferably between about 10-20 μm. Surface 420' of thinned wafer 412' and surface 490' of thinned substrate 456' may optionally be provided with a shallow hydrogen implant and prepared for covalent bonding for example by sputter etching the surface oxide in a neutralized plasma as known in the art (see for example C. Flötgen in ECS Trans. 64, 103 (2014), the entire disclosure of which is hereby incorporated by reference). Referring now to FIG. 6G, in a seventh step, thinned substrate 456' or thinned CMOS wafer 412' is flipped upside down, such that surfaces 420' and 490' prepared for wafer bonding face each other to be joined in covalent bond 450 in an eighth step (FIG. 6H) after an optional pre-bonding anneal prior to the removal of the surface oxide. Optional pre- and post-bonding annealing steps are both carried out at low temperature. Annealing temperatures may range between 100° C. and 200° C., or between 200° C. and 300° C., or between 300° C. and 400° C. In any case, they must be below about 450° C. in order to avoid disintegration of the metallization of CMOS processed wafer 412'. The optional post-bonding anneal may help in eliminating any interfacial barriers blocking electrical charge transport across the bonding interface, for example by causing optionally implanted hydrogen to passivate the dangling bonds so that ohmic behavior is attained. After the optional post-bonding anneal handling wafer 480 is removed in a ninth step (FIG. 6I), whereby surfaces 434 of absorber patches 452 is again exposed. Referring now to FIG. 6J, in a tenth step, surfaces 434 of absorber patches 452 may be subjected to an optional cleaning step to remove the bonding residues of handling wafer 480. Subsequently, trenches 454 may be optionally be filled by filling material 472' unless said trenches have already been filled by filling material 472 in the second step (FIG. 6B). Referring now to FIG. 6K, in an eleventh step, complete pixel detector 410 is finally obtained by metallizing surfaces 434 of absorber patches 452 with metal layer 432 acting as a metallic contact to which high voltage lead 430 may be attached to deplete drift regions 428', 456' and absorber 418.

Fabrication 400 may be the most preferred fabrication method of pixel detector 410 for absorber layers 418 which are both lattice and thermally mismatched with the Si substrate 456. The preferred material of absorber layers 418 may be a $Si_{1-x}Ge_x$ alloy which may preferably have a Ge content above 20%. A $Si_{1-x}Ge_x$ alloy with a high Ge content x of about $0.6 \leq x \leq 0.8$ may be an especially suitable alloy for absorber layer 418. Absorber layers with a thickness of 100-200 μm made from $Si_{1-x}Ge_x$ alloys with high Ge content are especially well suited for applications limited to X-ray energies below 40 keV, such as mammography applications. The most preferred $Si_{1-x}Ge_x$ alloy may be compositionally graded to a high Ge content x of about $0.6 \leq x \leq 0.8$ and optionally have a cap region of constant composition substantially equal to the final composition of the graded part, which may for example be graded linearly. In the most preferred fabrication 400 of pixel detector 410, interface 458 between Si substrate 456 and pixelated absorber 418 is substantially defect-free. This may for example be achieved by choosing width $w_3$ of semiconductor patches 452 forming pixelated absorber 418 and the grading rate both sufficiently small to permit elastic relaxation of the misfit stress during the epitaxial growth of absorber 418 as proven to be effective in the simpler example of step graded SiGe nanostructures (see for example M. Salvalaglio et al., in J. Appl. Phys. 116, 104306 (2014), and F. Isa et al. in Acta Materialia 114, 97 (2016), the entire disclosures of which are hereby incorporated by reference). The grading rate may preferably be chosen below about 3%, or below about 2%, or even below 1%. In other aspects of the embodiment, interface areas 458 between substrate 456 and patches 452 of pixelated absorber 418 may not be substantially defect-free, but of sufficiently small size to keep dark currents at acceptable levels, when a large voltage 430 is applied to metallized back contact 432 of absorber 418 and implants 438 of thinned CMOS processed wafer 412'. Such small interface regions are commonly employed for example in techniques of aspect ratio trapping (ART), wherein threading dislocations are trapped at the sidewalls of windows in a dielectric mask into which a semiconductor is selectively grown (see for example I. Åberg et al., in IEDM 2014, the entire disclosure of which is hereby incorporated by reference). With the help of ART also other absorber materials may be used apart from SiGe, such as GaAs, Ge, CdTe or CdZnTe.

Figure 7A:
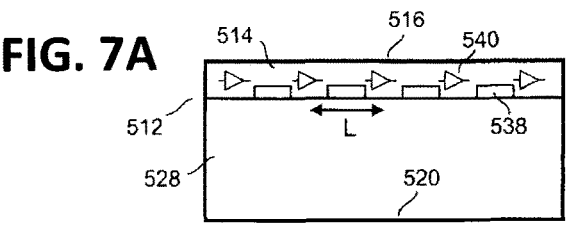
FIG. 7A is a cross-sectional view of a CMOS processed wafer with a readout unit.
Figure 7B:
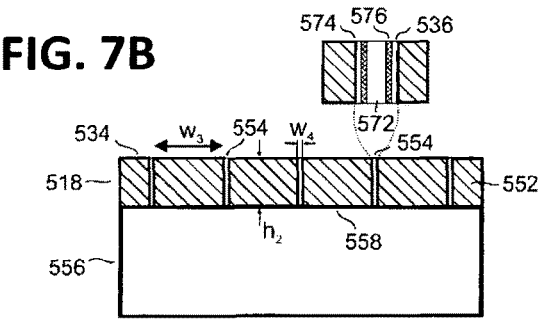
FIG. 7B is a cross-sectional view of a wafer with a pixelated and passivated epitaxial absorber layer.

Referring now to FIGS. 7A-7H, alternative fabrication 500 of monolithic pixel detector 510, may include the following steps, although not necessarily executed in the order shown. Referring now to FIG. 7A, in a first step, Si wafer 512 with front side 516 and backside 520, which may for example be lightly n-doped or lightly p-doped with a resistivity preferably above 500 Ωcm, is CMOS processed to obtain readout electronics 514, part 540 of which may be contained in every pixel of size L, defined by the spacing of charge collection implants 538. Referring now to FIG. 7B, in a second step, Si wafer 556 may be patterned and cleaned in order to serve as a substrate for absorber 518 to be epitaxially grown in the form of distinct patches 552 forming interface 558 with Si substrate 556. Patches 552 have width $w_3$ and height $h_2$ and are separated by trenches 554 of width $w_4$. The width $w_3$ of distinct absorber patches 552 may be larger, equal or smaller than the pixel size L defined by implants 538. The height of absorber patches 552 may be about 20-50 μm or preferably about 50-100 μm or even more preferably about 100-200 μm. The width $w_4$ of trenches may be below 1 μm or below 200 urn or even below 100 nm, when a self-limited epitaxial growth process and deeply patterned substrates are used to define the size $w_3$ of absorber patches 552 as known in the art (see for example International Patent Application No. WO 2011/135432 to von Känel, the entire disclosure of which is hereby incorporated by reference). Alternatively, when a method of ART is used to define the size $w_3$ of absorber patches 552, the width of trenches $w_4$ may be defined by the spacing of dielectric windows, which may be as narrow as the minimum width achievable by the lithography and deep reactive ion etching techniques known in the art (see for example X. Li et al., in Sensors and Actuators A87, 139 (2001) and E. H. Klaassen, in Sensors and Actuators A52, 132 (1996), the entire disclosure of which are hereby incorporated by reference). After the epitaxial growth sidewalls 574 of distinct patches 552 may optionally be passivated by a dielectric passivation layer. The passivation layer may comprise for example first dielectric layer 536 designed to control surface leakage along sidewalls 574 when pixel detector 510 is in operation. First dielectric layer may be a thermal oxide or an oxide formed by atomic layer deposition (ALD). The passivation layer may optionally comprise second dielectric layer 576, which may provide additional protection of sidewalls 574 against environmental influences. It may for example be made of $Al_2O_3$ which may be deposited by atomic layer deposition as known in the art. Trenches 554 may additionally be filled by dielectric filling material 572 to provide stability in an optional step of chemical mechanical polishing as a preparation of absorber surface 534 for a subsequent covalent wafer bonding step.

Figure 7C:
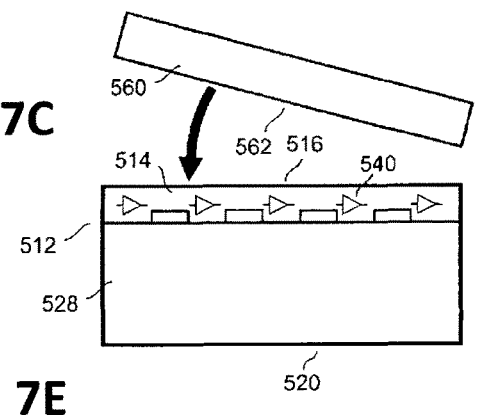
FIG. 7C is a cross-sectional view of a CMOS processed wafer with a readout unit and a handling wafer.
Figure 7D:
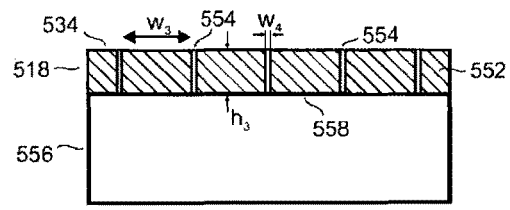
FIG. 7D is a cross-sectional view of a wafer with a pixelated and passivated epitaxial absorber layer after chemical mechanical polishing.
Figure 7G:
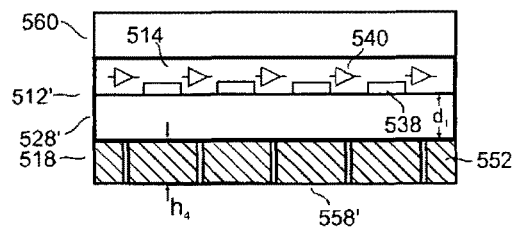
FIG. 7G is a cross-sectional view of a thinned CMOS processed wafer bonded to a pixelated epitaxial absorber layer after substrate removal.
Figure 7F:
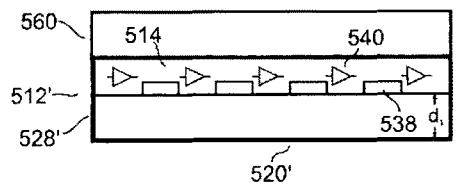
FIG. 7F is a cross-sectional view of a thinned CMOS processed wafer bonded to a pixelated epitaxial absorber layer.
Figure 7H:
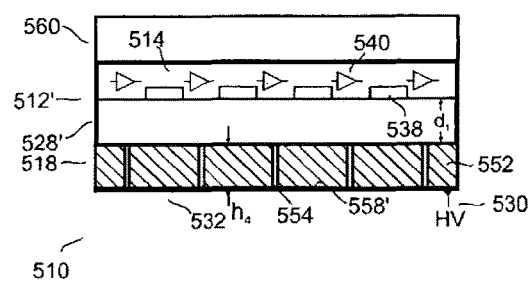
FIG. 7H is a cross-sectional view of a thinned CMOS processed wafer with a readout unit bonded to a pixelated epitaxial absorber layer after substrate removal and electrical contact formation.
Figure 7E:
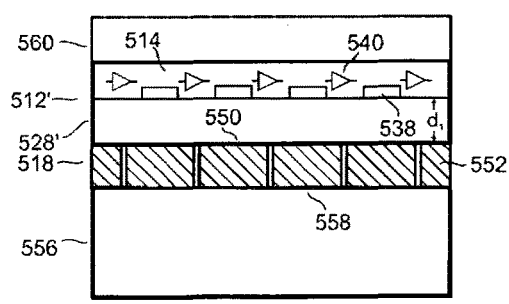
FIG. 7E is a cross-sectional view of a thinned CMOS processed wafer bonded to a handling wafer.

Referring now to FIG. 7C, in third step, surface 516 of Si wafer 512 may undergo an optional chemical mechanical polishing step before being bonded to surface 562 of handling wafer 560 as a means to provide mechanical stability in the subsequent thinning of drift region 528 for example in a chemical mechanical polishing step. Referring now to FIG. 7D, in a fourth step, surface 534 of epitaxial absorber 518 may subjected to a chemical mechanical polishing step whereby the height of epitaxial absorber may be slightly reduced for example by 1-4 μm to the height $h_3$. Referring now to FIG. 7E, in a fifth step, drift region 528 of CMOS processed wafer 512 is thinned for example in a plasma etching or chemical mechanical polishing step. Thinned wafer 512' with drift region 528' thereby assumes a thickness $d_1$ which is preferably between about 10-100 μm, and even more preferably between about 10-20 μm. In a sixth step surface 520' of thinned wafer 512' and surface 534 of absorber 518 may optionally be provided with a shallow hydrogen implant and prepared for covalent bonding for example by sputter etching the surface oxide in a neutralized plasma as known in the art (see for example C. Flötgen in ECS Trans. 64, 103 (2014), the entire disclosure of which is hereby incorporated by reference) and joined in covalent bond 550 after an optional pre-bonding anneal (FIG. 7F). Covalent bond 550 may then be subjected to an optional post-bonding anneal. Optional pre- and post-bonding annealing steps are both carried out at low temperature. Annealing temperatures may range between 100° C. and 200° C., or between 200° C. and 300° C., or between 300° C. and 400° C. In any case they must be below about 450° C. in order to avoid disintegration of the metallization of CMOS processed wafer 512'. The optional post-bonding anneal may help in eliminating any interfacial barriers blocking electrical charge transport across the bonding interface, for example by causing optionally implanted hydrogen to passivate the dangling bonds so that ohmic behavior is attained. After the optional post-bonding anneal substrate 556 of epitaxial absorber 518 may be removed in a seventh step (FIG. 7G), either by a chemical mechanical polishing or a plasma etching step to expose surfaces 558' of absorber patches 552. It may be advantageous to etch away also part of absorber patches 552 during this etching step to reduce their height to ha, especially if their interface with substrate 512, 512' is not defect-free. Height $h_4$ may be smaller by a few μm than height $h_3$, so that in addition to misfit dislocations also threading dislocations are removed in this etching step. Referring now to FIG. 7H, in an eighth step, complete pixel detector 510 is finally obtained by metallizing surfaces 558' of absorber patches 552 with metal layer 532 acting as a metallic contact to which high voltage lead 530 may be attached to deplete drift regions 528 and absorber 518.

Fabrication 500 of pixel detector 510 has the advantage that only the thickness $d_1$ of thinned drift region 528' along with the height $h_4$ of absorber patches 552 need to be depleted during detector operation. It may also be a preferred fabrication method of pixel detector 510 for absorber layers 518 which are both lattice and thermally mismatched with the Si substrate 556. The preferred material of absorber layers 518 may be a $Si_{1-x}Ge_x$ alloy which may preferably have a Ge content above 20%. A $Si_{1-x}Ge_x$ alloy with a high Ge content x of about $0.6 \leq x \leq 0.8$ may be an especially suitable alloy for absorber layer 518. Absorber layers with a thickness of 100-200 μm made from $Si_{1-x}Ge_x$ alloys with high Ge content are also especially suited for applications limited to X-ray energies below 40 keV, such as mammography applications. The most preferred $Si_{1-x}Ge_x$ alloy may be compositionally graded to a high Ge content x of about $0.6 \leq x \leq 0.8$ and optionally have a cap region of constant composition substantially equal to the final composition of the graded part, which may for example be graded linearly. In the most preferred fabrication 500 of pixel detector 510 interface 558 between Si substrate 556 and pixelated absorber 518 is substantially defect-free. This may for example be achieved by choosing width $w_3$ of semiconductor patches 552 forming pixelated absorber 518 and the grading rate both sufficiently small to permit elastic relaxation of the misfit stress during the epitaxial growth of absorber 518 as proven to be effective in the simpler example step graded SiGe nanostructures of (see for example M. Salvalaglio et al., in J. Appl. Phys. 116, 104306 (2014), and F. Isa et al. in Acta Materialia 114, 97 (2016), the entire disclosures of which are hereby incorporated by reference). The grading rate may preferably be chosen below about 3%, or below about 2%, or even below 1%. In other aspects of the embodiment interface areas 558 between substrate 556 and patches 552 of pixelated absorber 518 may not be substantially defect-free, but of sufficiently small size to keep dark currents at acceptable levels, when a large voltage 530 is applied to metallized back contact 532 of absorber 518 and implants 538 of thinned CMOS processed wafer 512'. As known to one skilled in the art, such small interface regions are commonly employed for example in techniques of aspect ratio trapping (ART), wherein threading dislocations are trapped at the sidewalls of windows in a dielectric mask into which a semiconductor is selectively grown (see for example I. Åberg et al., in IEDM San Francisco, 2010, the entire disclosure of which is hereby incorporated by reference). With the help of ART also other absorber materials may be used apart from SiGe, such as GaAs, Ge, CdTe or CdZnTe.

Exemplary Applications of Photon Counting CBCT with Monolithic CMOS Integrated Pixel Detector The CBCT of the present invention is integrated into and used in methods of the following medical applications, either human or veterinary, and other applications as described below.

Projection Radiography Example

The CBCT of the invention is used as a digital radiography system in which the X-rays transmitted through an object are converted into electrical signals in the FPD, generating digital information, which is transmitted and converted into an image displayed on a computer screen either locally or remotely.

There are many disease states in which classic diagnosis is obtained by plain radiographs, in combination with systems and methods incorporating the CBCT of the present invention. Examples of systems and method include those to diagnose various types of arthritis and pneumonia, bone tumors, fractures, congenital skeletal anomalies, and the like.

Interventional Radiology Example

The introduction of the monolithic CMOS integrated pixel FPD allows for the replacement of the cesium iodide (CsI) screen in fluoroscope designs. Therefore "four dimensional CT" (4DCT) is more accurate than "fluoroscopy" to define the CBCT of the invention even if the field of applications is the same. The photon counting CBCT with monolithic CMOS integrated pixel detectors allows real-time imaging of anatomical structures in motion, and the method is optionally augmented with a radio-contrast agent. Radio-contrast agents are administered by swallowing or injecting into the body of the patient to delineate anatomy, function of the blood vessels and various systems, e.g. the genitor-urinary system or the gastro-intestinal tract. Two radio-contrast agents are presently in common use. Barium sulfate (BaSO4) is administered to the subject orally or rectally for evaluation of the gastro-intestinal tract. Iodine in various formulations is given by oral, rectal, intra-arterial or intravenous pathways. These radio-contrast agents absorb or scatter X-rays, and in conjunction with real-time imaging, permit the imaging of dynamic physiological processes in the digestive tract or blood flow in the vascular system. Iodine contrast agents are also concentrated in abnormal areas in different concentrations than in normal tissues to make abnormalities (e.g. tumors, cysts, inflamed areas) visible.

More generally, the CBCT is used in interventional radiology systems and methods. Interventional radiology includes minimally invasive procedures that are guided by imaging systems utilizing systems and methods having the FPD described herein. These procedures are diagnostic or involve treatments, such as angiographic intervention and the systems used therewith. Exemplary systems include those procedures to diagnose and/or treat peripheral vascular disease, renal artery stenosis, inferior vena cava filter placement, gastrostomy tube placement, biliary stent intervention, and hepatic intervention. Non-angiographic procedures such as image guided orthopedic, thoracic, abdominal, head and neck, and neuro surgery, biopsies, brachytherapy or external beam radiotherapy, percutaneous drain and stent placement or radiofrequency ablation are also included. Images created with the assistance of the systems utilizing the pixel detector are used for guidance. The images created with the assistance of the photon counting FPD provide maps that permit the interventional radiologist to guide instruments through the body of a subject to the areas containing disease conditions. These systems and methods minimize the physical tissue trauma to the subject, reduce infection rates, recovery times, and hospitalization stays, such as in angiographic interventions, or non-angiographic procedures like image guided orthopedic, thoracic, abdominal, head and neck, and neuro surgery, biopsies, brachytherapy or external beam radiotherapy, percutaneous drain and stent placement or radiofrequency ablation.

Addendum

The following US patent documents, foreign patent documents, and Additional Publications are incorporated herein by reference thereto and relied upon:

US Patent Documents

| 5,712,484 |    | January 1998   | Harada et al.    |
|-----------|----|----------------|------------------|
| 6,787,885 | B2 | September 2004 | Esser et al.     |
| 8,237,126 | B2 | August 2012    | von Känel et al. |
| 8,378,310 | B2 | February 2009  | Bornefalk et al. |
| 8,792,965 | B2 | July 2014      | Ning et al.      |

Other Patent Documents

| EP0571135    | A2 | November 1993 | Collins et al.    |
|--------------|----|---------------|-------------------|
| WO02/067271  | A2 | August 2002   | Ruzin             |
| EP1691422    | A1 | August 2006   | Yasuda et al.     |
| WO2006117720 | A2 | November 2006 | Proksa et al.     |
| WO2011102779 | A1 | August 2011   | Danielsson et al. |
| WO2011/135432| A1 | November 2011 | von Känel et al.  |
| WO2014123726 | A1 | August 2014   | Ning et al.       |

Additional Publications
http://medipix.web.cern.ch
http://www.canberra.com/products/detectors/germanium-detectors.asp
http://www.dectris.ch
http://www.healthcare.philips.com/

Alig R. C. et al., "Scattering by ionization and phonon emission in semiconductors", Physical Review B 22, 5565 (1980)

Alig R. C. "Scattering by ionization and phonon emission in semiconductors. II. Monte Carlo calculations", Physical Review B 27, 968 (1983)

Baba R. et al.: Comparison of flat-panel detector and image-intensifier detector for cone-beam CT, Comp. Med. Imaging and Graphics 26, 153 (2002)

Bale D. S. et al.: Nature of polarization in wide-bandgap semiconductor detectors under high-flux irradiation: Application to semi-insulating Cd1-xZnxTe, Phys. Rev. B 77, 035205 (2008)

Ballabriga R. et al. "The Medipix3RX: a high resolution, zero dead-time pixel detector readout chip allowing spectroscopic imaging", 2013, JINST 8 C02016

Bertolucci E. et al.: GaAs pixel radiation detector as an autoradiography tool for genetic studies, Nucl. Sci. Meth. Phys. Res. A 422, 242 (1999)

Bornefalk H./Danielsson M.: Photon-counting spectral computed tomography using silicon strip detectors: a feasibility study, Phys. Med. Biol. 55, 1999 (2010)

Cho Hyo-Min et al., «Characteristic performance evaluation of a photon counting Si strip detector for low dose spectral breast CT imaging», Med. Phys. September 2014; 41 (9), 091903

Colace L. et al., "Low Dark-Current Germanium-on-Silicon Near-Infrared Detectors", IEEE Photonics Technology Letters 19, 1813-1815 (2007)

Falub C. V. et al., "Perfect crystals grown from imperfect interfaces", Scientific Reports 3, 2276 (2013)

Fitzgerald E. A. et al.: Totally relaxed $Ge_xSi_{1-x}$ layers with low threading dislocation densities grown on Si substrates, Appl. Phys., Letter 59, 811 (1991)

Flötgen C. et al., "Novel surface preparation methods for covalent and conductive bonded interfaces fabrication", ECS Transactions 64, 103-110 (2014)

Gros d'Aillon E. et al.: Development and characterization of a 3D GaAs X-ray detector for medical imaging, Nucl. Instr. Meth. Phys. Res. A 727, 126 (2013)

Gupta R. et al.: Ultra-high resolution flat-panel volume CT: fundamental principles, design architecture, and system characterization, Eur. Radiol. 16, 1191 (2006)

Hamann E. et al.: Performance of a Medipix3RX Spectroscopic Pixel Detector with a High Resistivity Gallium Arsenide Sensor, IEEE Trans. Med. Imaging 34, 707, (2015)

Henry D. et al.: TSV Last for Hybrid Pixel Detectors: Application to Particle Physics and Imaging Experiments, in IEEE Electronic Components & Technology Conference, 568 (2013)

Hirota S. et al.: Cone-Beam CT with Flat-Panel-Detector Digital Angiography System: Early Experience in Abdominal Interventional Procedures, Cardiovasc. Intervent. Radiol. 29, 1034 (2006)

Isa F. et al.: From plastic to elastic stress relaxation in highly mismatched SiGe/Si Heterostructures, Acta Materialia 114, 97-105 (2016)

Jiang T. et al., "Hydrogenation of interface states at a clean grain boundary in the direct silicon bonded wafer Phys. Stat. Sol. A 209, 990-993 (2012)

Kasap S. et al., "Amorphous and polycrystalline photoconductors for direct conversion flat panel X-ray image sensors", Sensors 11, 5112-5157 (2011)

Klaassen E. H. et al.: "Silicon fusion bonding and deep reactive ion etching: a new technology for microstructures", Sensors and Actuators A52, 132-139 (1996)

Kreiliger T. et al., "Individual heterojunctions of 3D germanium crystals on silicon CMOS for monolithically integrated X-ray detector", Physica Status Solidi A 211, 131-135 (2014)

Liu X. et al.: A Silicon-Strip Detector for Photon-Counting Spectral CT: Energy Resolution From 40 keV to 120 keV, IEEE Transactions on Nuclear Science, vol. 61, issue 3, pp. 1099-1105 (2014)

Loshachenko A. et al., "Impact of hydrogen on electrical levels and luminescence of dislocation network at the interface of hydrophilically bonded silicon wafers", Phys. Stat. Sol. C 10, 36 (2013)

Mattiazzo S. et al., "LePIX: First results from a novel monolithic pixel sensor", Nuclear Instruments and Methods in Physics Research A 718, 288-291 (2013)

Orth R. C. et al.: C-arm Cone-beam CT: General Principles and Technical Considerations for Use in Interventional Radiology, J. Vasc. Interv. Radiol. 19, 814 (2008)

Pennicard D. et al.: Development of LAMBDA: Large Area Medipix-Based Detector Array, 2012 JINST 6 C11009

Procz S. et al. "Medipix3 CT for material sciences", 2013 JINST 8 C01025

Salvalaglio M. et al., "Fine control of plastic and elastic relaxation in Ge/Si vertical heterostructures", Journal of Applied Physics 116, 104306 (2014)

Sechopoulos I. "A review of breast tomosynthesis" Med Phys. 2013 January; 40(1):014302

Taguchi K./Iwanczyk J.: "Vision 20/20: Single photon counting x-ray detectors in medical imaging", Med Phys. October 2013; 40(10) 100901

Veale, M. C. et al.: Chromium compensated gallium arsenide detectors for X-ray and γ-ray spectroscopic imaging, Nucl Instr. Meth. Phys. Res, A 752, 6 (2014)

Vykydal Z. et al. in Nucl. Instr. Meth. in Phys. Res. A 591, 241 (2008)

Weber J. et al., "Near-band-gap photoluminescence of Si—Ge alloys", Physical Review B 40, 5683-5693 (1989)

Germanium Detectors

Figure 8:
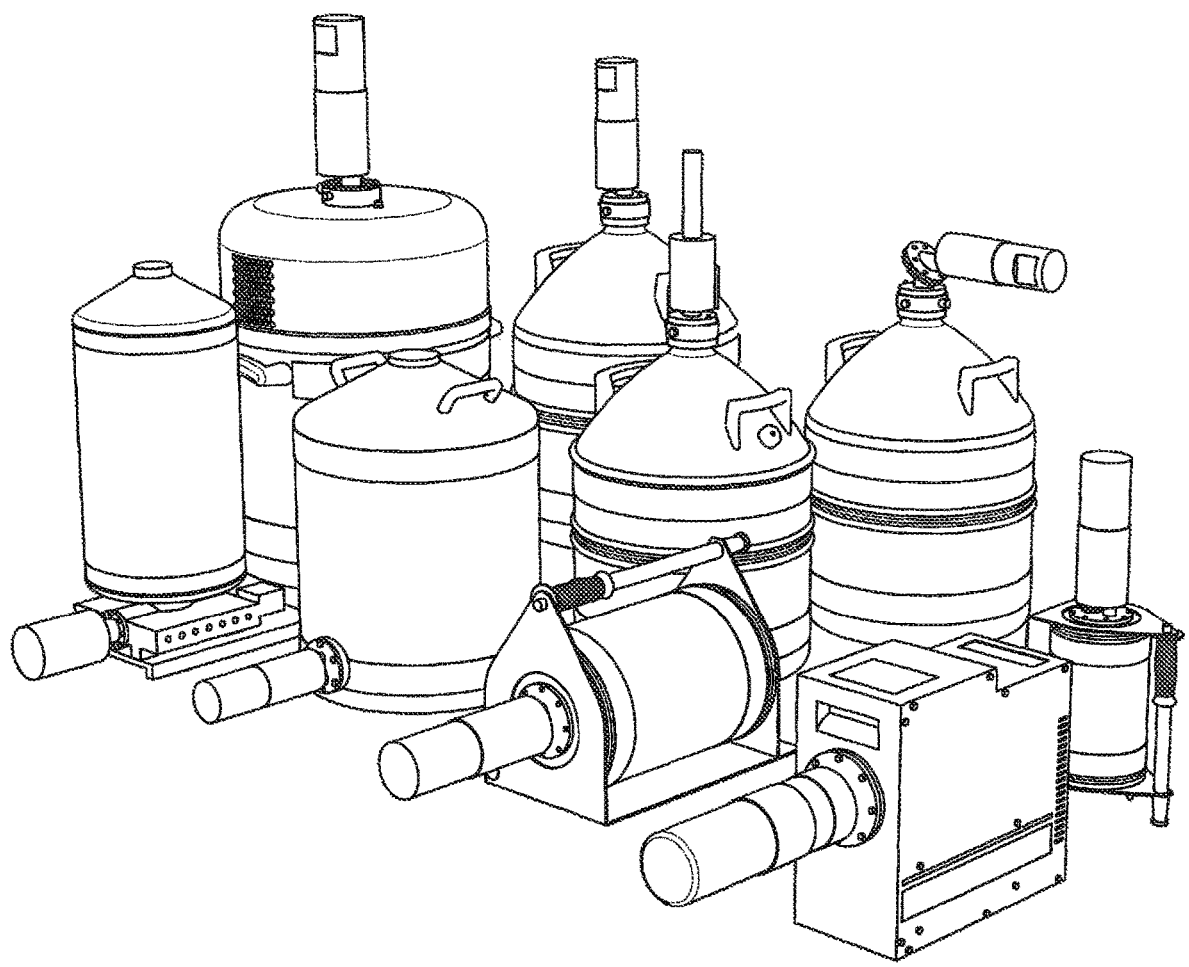
FIG. 8 shows examples of Germanium Detectors in a perspective view.

FIG. 8 shows examples of Germanium Detectors in a perspective view.

Introduction

Germanium detectors are semiconductor diodes having a p-i-n structure in which the intrinsic (i) region is sensitive to ionizing radiation, particularly x rays and gamma rays. Under reverse bias, an electric field extends across the intrinsic or depleted region. When photons interact with the material within the depleted volume of a detector, charge carriers (holes and electrons) are produced and are swept by the electric field to the p and n electrodes. This charge, which is in proportion to the energy deposited in the detector by the incoming photon, is converted into a voltage pulse by an integral charge sensitive preamplifier.

Figure 9:
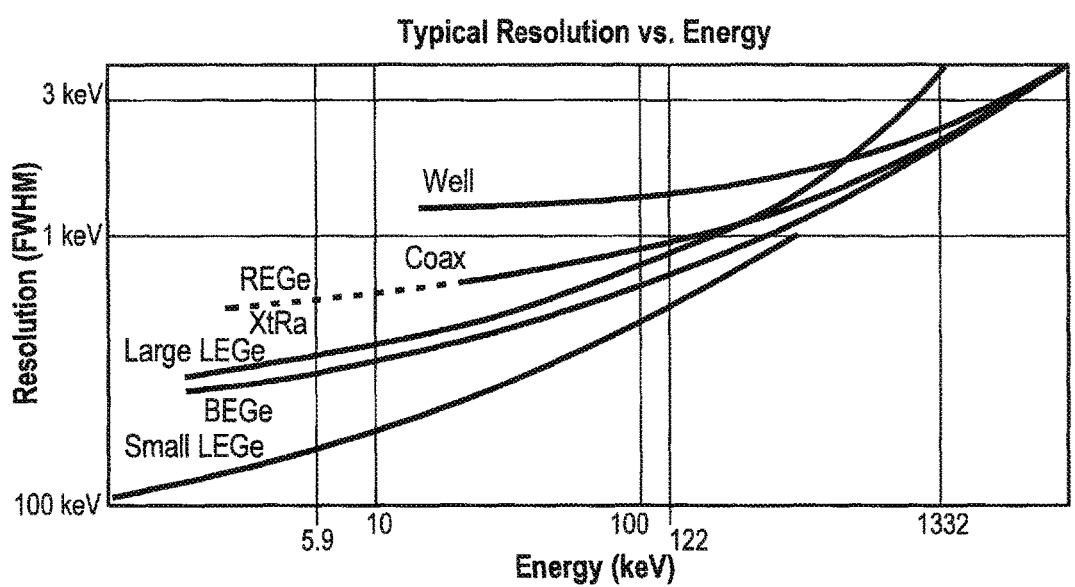
FIG. 9 shows a diagram illustrating 'Typical Resolution vs. Energy'.

Because germanium has relatively low band gap, these detectors must be cooled in order to reduce the thermal generation of charge carriers (thus reverse leakage current) to an acceptable level. Otherwise, leakage current induced noise destroys the energy resolution of the detector. FIG. 9 shows a diagram illustrating 'Typical Resolution vs. Energy'. Liquid nitrogen, which has a temperature of 77° K is the common cooling medium for such detectors. The detector is mounted in a vacuum chamber which is attached to or inserted into an LN2 Dewar. The sensitive detector surfaces are thus protected from moisture and condensible contaminants.

Germanium Detectors

Types of Germanium Detectors

CANBERRA offers the widest choice of detector types in the industry. Employing the appropriate technology in both materials and processing techniques, CANBERRA can offer the optimum detector for a wide range of applications. We use both p-type and n-type germanium and we use diffused, implanted, and barrier contacts to achieve this product variety.

Cryostats

The liquid nitrogen cryostat is the most important, and perhaps the least appreciated, component in assuring reliable long term performance of a Ge detector system. CANBERRA manufactures its own cryostats to exacting quality standards to ensure long detector life under the harshest operating conditions.

The standard CANBERRA cryostat is our Slimline Design in which the detector chamber and preamplifier are packaged together in a compact cylinder.

Low energy detectors, such as the Ultra-LEGes and Si(Li)s use our flanged cryostats which are compatible with the small diameter (25 mm) endcaps associated with this type of detector. Flanged cryostats are available as an extra-cost option for other detector types.

CANBERRA also offers a line of convertible cryostats which, in conjunction with detectors packaged in small vacuum chambers, can be reconfigured in the field.

For applications requiring liquid nitrogen free operation, CANBERRA offers the Cryolectric II. This electrically cooled cryostat uses a CFC-free refrigerant and is well suited for use in industrial and laboratory applications.

FIG. 10 shows information about 'Structure Code' and 'Detector Type'.

Figures 11, 12:
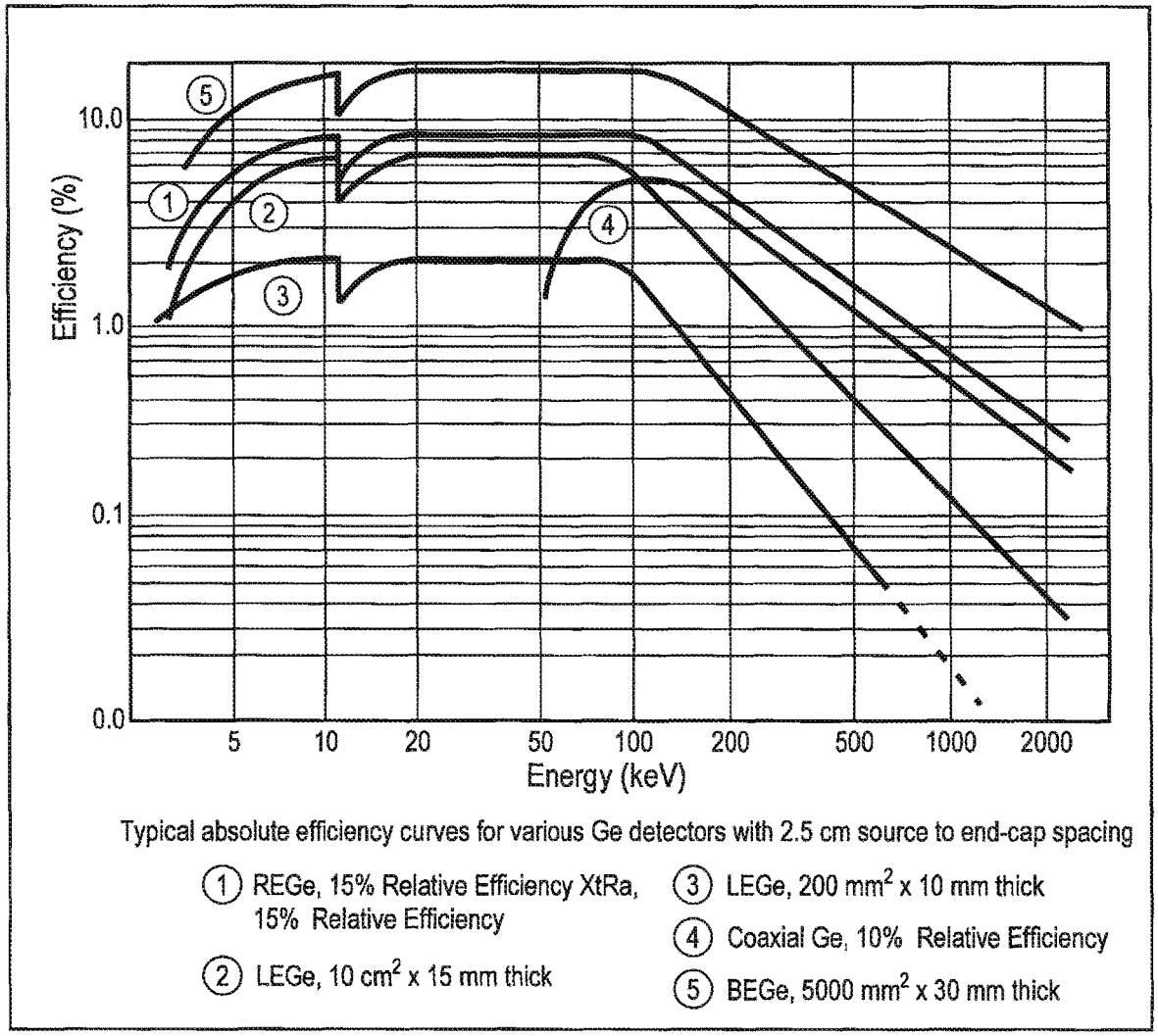
FIG. 11 shows a diagram illustrating 'Typical absolute efficiency curves for various Ge detectors with 2.5 cm source to end-cap spacing'.
FIG. 12 shows actual performance data on a typical detector.

FIG. 11 shows a diagram illustrating 'Typical absolute efficiency curves for various Ge detectors with 2.5 cm source to end-cap spacing'.

Germanium Detectors

Preamplifiers

There are only two basic types of preamplifiers in use on Ge detectors. These are charge sensitive preamplifiers, which employ either dynamic charge restoration (RC feedback), or pulsed charge restoration (Pulsed optical or Transistor reset) methods to discharge the integrator. The following figure illustrates the energy rate limitation of decoupled RC feedback preamps, which is a function of the feedback resistor value and the dynamic output voltage range of the integrator, which is limited to about 20 volts.

The energy rate limit can be increased very substantially by choosing a lower value feedback resistor with, of course, an accompanying increase in noise. FIG. 12 shows actual performance data on a typical detector.

Pulsed-Optical Reset preamplifiers are widely used on low energy detectors where resolution is of utmost consideration. Eliminating the feedback resistor decreases noise without a serious impact on dead time, so long as the average energy per event is low to moderate. At 5.9 keV/event, a CANBERRA 2008 preamp may process almost 1000 pulses between resets Since the reset recovery time is 2-3 amplifier pulse widths, little data is lost in this situation. Optical feedback systems can, however, exhibit long recovery times due to light activated surface states in the FET. Proper selection and treatment of components can minimize the problem, but it is generally present to some degree in pulsed-optical systems. With high energies where resets necessarily occur very often, perhaps after as few as 10 events, this spurious response can be a serious problem. As a consequence, pulsed-optical feedback systems are not generally used with coaxial detectors.

The Transistor Reset Preamp was developed in an attempt to overcome the problems associated with Pulsed-Optical Reset Preamps in high energy, high rate systems. The feedback capacitor is discharged by means of a transistor switch connected to the FET gate This transistor adds some capacitance and noise to the input circuit, but this is tolerable in most applications involving high count or energy rates. Compared to an RC preamplifier with selected feedback resistor for high rate performance, the Transistor Reset Preamplifier will exhibit less noise but will sacrifice dead time because the amplifier will require 2-3 pulse widths to recover from the periodic reset of the preamplifier. Thus, in applications demanding high throughput rates, the Transistor Reset Preamp is not a good choice. It can be used in situations where the energy rate is so high that an RC preamp might saturate—but the throughput rate may be diminishingly small in this case.

Systems

In addition to the NIMs MCAs, and Computer Systems that are described elsewhere in this catalog CANBERRA offers many options and accessories that are designed to complement our line of germanium detectors. Below is a partial listing of the equipment and systems that we offer. Some of these systems are described in separate specification sheets and brochures while others are custom tailored. We stand ready to propose and supply systems that will meet your specific requirements. Contact your local CANBERRA representative or the factory, describing your problem or application, and we will send you a proposal immediately.

Accessories

Liquid nitrogen supply Dewars

LN2 transfer devices

Automatic LN2 transfer systems

LN2 level alarms

Lead shields for low level counting

Compton suppression spectrometers

Welcome to the Medipix Homepage!

Figure 13:
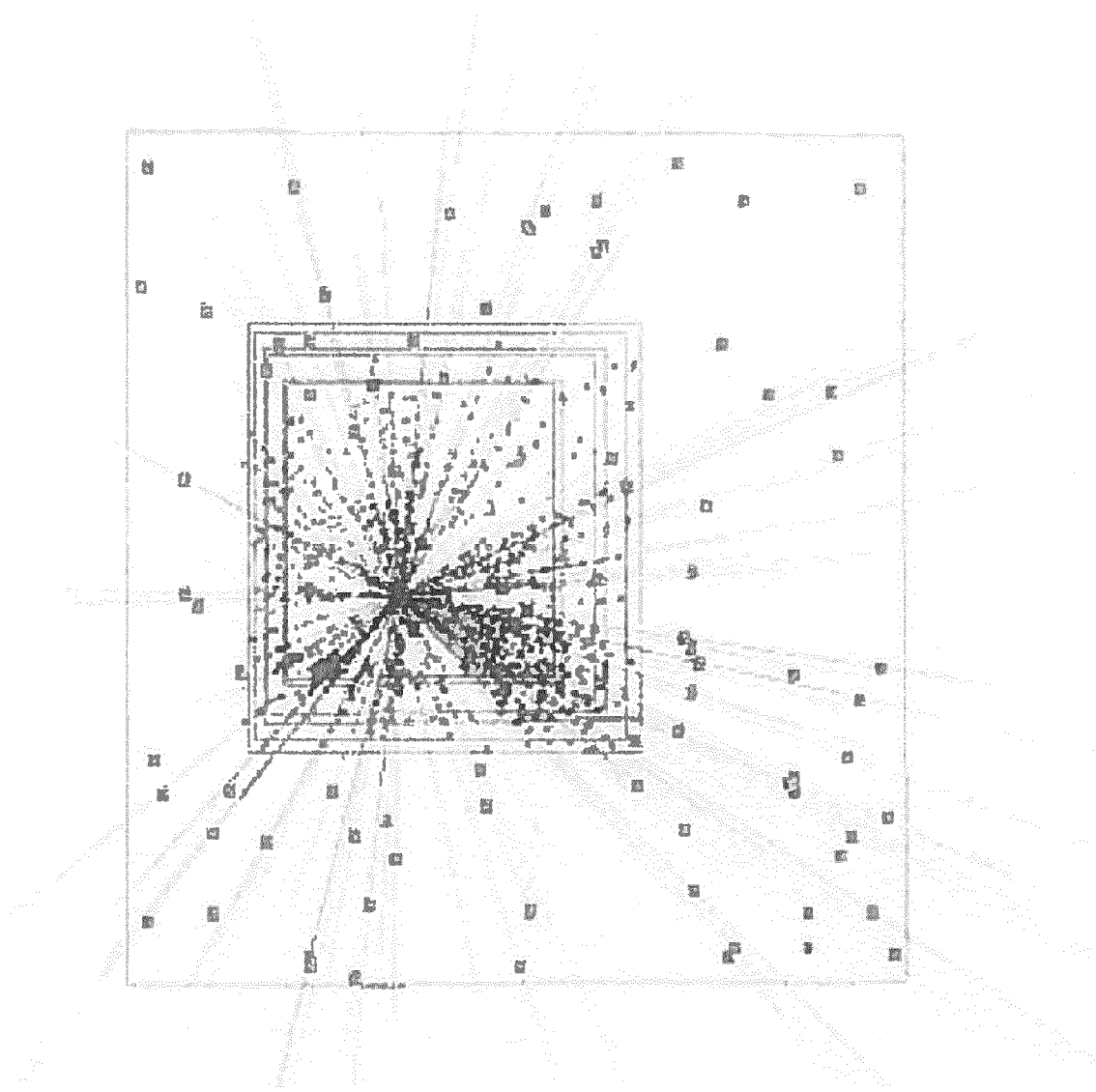
FIG. 13 shows the image which demonstrated the potential of hybrid silicon pixel detectors for tracking applications in High Energy Physics.

FIG. 13 shows the image which demonstrated the potential of hybrid silicon pixel detectors for tracking applications in High Energy Physics. It shows 153 high energy particle tracks flying through a telescope of half a million pixels in the WA97 experiment back in 1995. Every red dot in this image signifies a pixel which has been hit by a track and there are no pixels giving false hits. Therefore this image— which was taken with a 1 microsecond shutter time—is noise free! That was the key parameter which drove almost all of the LHC experiments to adopt hybrid pixel technology for their vertex detectors. It is also why this technology is so unique for imaging applications.

With the Medipix family of chips we have striven to disseminate a technology which was developed because of the needs of the Large Hadron Collider experiments at CERN to other fields of science.

The activity started in the 90's when a small Collaboration of 4 institutes produced the Medipix1 or Photon Counting Chip (PCC) demonstrating the potential of the new technology to provide noise-free single photon counting.

At the end of the 1990's the Medipix2 Collaboration was formed with the aim of taking advantage of the potential of deep sub-micron CMOS to shrink the pixel size and to increase the number of pixels per chip. The Medipix2 chip is the outcome of that effort.

During the extensive characterisation of that chip we recognised that charge diffusion within the sensor ultimately limits the performance of the chip for small pixel sizes. With access to very deep sub-micron CMOS processes it is now possible to mitigate the effects of charge diffusion by allowing pixels to communicate with each other on an event-by-event basis. Moreover is becomes possible to integrate 2 counters on a single small pixel permitting one image to be taken while the previous one is being read out. This is what the Medipix3 Collaboration hopes to achieve.

What is claimed is:

1. A cone beam computer tomography (CBCT) system, comprising
   a. at least one X-ray source, and a monolithic flat panel detector (FPD) disposed for the direct detection of X-ray radiation comprising at least one buttable monolithic detector comprising a covalent wafer bond between at least one absorber wafer made from single crystal material and a backside of at least one thin CMOS processed readout wafer configured so that the backside of the at least one readout wafer faces the radiation, the readout wafer comprising on its front side a readout unit communicating with implanted charge collectors on its front side defining a pixel size L wherein the implanted charge collectors are disposed to collect electric charges generated by X-rays incident on the at least one absorber wafer and drifting along electric field lines towards the charge collectors when the detector is in operation and wherein electrical signals induced by the charges are amplified, shaped and transformed into digital signals in the readout unit, and
   b. one or more devices providing data collection, computation and/or storage functionality, arranged and connected to receive the digital electrical signals from the readout unit of the FPD and to generate computed tomography images on at least one computer screen.

2. The system of claim 1, wherein the at least one X-ray source and the FPD are mounted on a C-arm permitting interventional radiology.

3. The system of claim 1, wherein the at least one X-ray source and the FPD are mounted on a C-arm permitting 3D imaging for mammography.

4. The system of claim 1, wherein the FPD and the one or more devices providing data collection are configured to provide photon counting capability to permit energy resolved single photon counting.

5. The system of claim 1, wherein the at least one thin readout wafer has a thickness of 10-100 µm.

6. The system of claim 1, wherein the at least one thin readout wafer has a thickness of 10-20 µm.

7. The system of claim 1, wherein the monolithic FPD comprises an oxide-free covalent wafer bond between the at least one absorber wafer and the backside of the at least one CMOS processed readout wafer.

8. The system of claim 1, wherein the FPD comprises buttable tiles and wherein the FPD comprises an area of at least 20×20 cm².

9. The system of claim 8, wherein the spacing between buttable tiles is in the range of 50-100 µm.

10. The system of claim 1, wherein the FPD is adapted to provide a spatial resolution in the range of 100-200 µm.

11. The system of claim 1, wherein the FPD is adapted to provide a spatial resolution in the range of 50-100 µm.

12. The system of claim 1, wherein the FPD is adapted to provide a spatial resolution in the range of 20-50 µm.

13. The system of claim 1, wherein the at least one X-ray source, FPD and the one or more devices providing data collection, computation and/or storage functionality are adapted for use in one of a group of applications consisting of projection radiography, mammography and interventional radiology.

14. The system of claim 1, wherein the at least one X-ray source, FPD and the one or more devices providing data collection, computation and/or storage functionality are adapted for use in mammography.

15. The system of claim 1, wherein the absorber wafer comprises at least one element with an atomic number larger than that of Si.

16. The system of claim 1, wherein the absorber wafer is made from at least one of a group of absorber materials consisting of Si, $Si_{1-x}Ge_x$ alloys with Ge fractions $0 \leq x \leq 1$, GaAs, CdTe, and $Cd_{1-x}Zn_x$Te with x of about 10%.

17. The system of claim 1, wherein the absorber wafer is made from a $Si_{1-x}Ge_x$ alloy with a Ge fraction of $0 \leq x \leq 1$.

18. The system of claim 17, wherein the absorber wafer comprises a 100-200 µm thick epitaxial layer on a Si substrate.

19. The system of claim 1, wherein the absorber wafer is made from a $Si_{1-x}Ge_x$ alloy with a Ge fraction of $0.6 \leq x \leq 0.8$.

20. The system of claim 19, wherein the absorber wafer comprises a 100-200 µm thick epitaxial layer on a Si substrate.

21. The system of claim 1, wherein the at least one thin CMOS processed readout wafer comprises implants on a front surface configured to receive the analog electrical signals generated by absorbed X-ray photons in the at least one absorber wafer, and wherein further circuitry amplifies, shapes and transforms these electrical signals into digital signals to be further processed in the one or more devices providing data collection, computation and/or storage functionality to be displayed as a computed tomography image on at least one computer screen.

22. A method for performing cone beam computer tomography (CBCT), the method comprising steps of
   a. providing at least one X-ray source;
   b. forming a monolithic FPD by covalently bonding at least one single crystal absorber wafer to at least one CMOS processed readout wafer;
   c. disposing the FPD and at least one device providing data collection, computation and storage functionality to provide single-photon counting capability;
   d. with the at least one X-ray source and the FPD mounted on a C-arm and a patient positioned in an appropriate operation position, activating the at least one readout wafer to communicate with the at least one device providing data collection, computation and storage functionality;
   e. disposing the at least one device to receive electrical signals from the FPD, and
   f. scanning the patient; and
   g. generating computed tomography images on at least one computer screen.

* * * * *